United States Patent
Yamanaka et al.

(10) Patent No.: US 11,859,229 B2
(45) Date of Patent: Jan. 2, 2024

(54) POLYVINYL ALCOHOL-DEGRADING ENZYME AND PROCESS FOR PRODUCING THE SAME

(71) Applicant: Hayashibara Co., Ltd., Okayama (JP)

(72) Inventors: Akihiro Yamanaka, Okayama (JP); Naoki Matsuo, Okayama (JP); Tetsuya Mori, Okayama (JP); Tomoyuki Nishimoto, Okayama (JP)

(73) Assignee: HAYASHIBARA CO., LTD., Okayama (JP)

(*) Notice: Subject to any disclaimer, the term of this patent is extended or adjusted under 35 U.S.C. 154(b) by 64 days.

(21) Appl. No.: 17/449,888

(22) Filed: Oct. 4, 2021

(65) Prior Publication Data

US 2022/0017934 A1   Jan. 20, 2022

Related U.S. Application Data

(62) Division of application No. 16/490,000, filed as application No. PCT/JP2018/006767 on Feb. 23, 2018, now abandoned.

(30) Foreign Application Priority Data

Mar. 2, 2017  (JP) ................................. 2017-039678

(51) Int. Cl.
  *C12P 21/02*   (2006.01)
  *C12N 9/14*    (2006.01)
  *C12N 15/11*   (2006.01)

(52) U.S. Cl.
  CPC ................ *C12P 21/02* (2013.01); *C12N 9/14* (2013.01); *C12N 15/111* (2013.01)

(58) Field of Classification Search
  CPC ......... C12P 21/02; C12N 9/14; C12N 15/111; C12Y 101/03018; C12Y 101/0303; C12Y 307/01007
  See application file for complete search history.

(56) References Cited

FOREIGN PATENT DOCUMENTS

| | | |
|---|---|---|
| EP | 1571202 B1 | 7/2009 |
| EP | 1621609 B1 | 12/2009 |
| EP | 1623959 B1 | 9/2010 |
| JP | H09-206079 A | 8/1997 |
| JP | H11-103861 A | 4/1999 |
| JP | 2004-000259 A | 1/2004 |
| JP | 2005-278639 A | 10/2005 |
| JP | 2006-042611 A | 2/2006 |
| JP | 2006-042612 A | 2/2006 |
| JP | 2006-180706 A | 7/2006 |
| JP | 2013-116959 A | 6/2013 |
| JP | 5891478 B2 | 3/2016 |
| WO | 2004/081212 A1 | 9/2004 |

OTHER PUBLICATIONS

Singh RK et al. Protein Engineering Approaches in the Post-Genomic Era. 2017. Current Protein and Peptide Science. 18, 1-11. (Year: 2017).*

Zhang M et al. Propagated Perturbations from a Peripheral Mutation Show Interactions Supporting WW Domain Thermostability. 2018. Structure. 26, 1474-1485 (Year: 2018).*

Shimao M et al. Cloning and Characterization of the Gene Encoding Pyrroloquinoline Quinone-dependent Poly(vinyl alcohol) Dehydrogenase of Pseudomonas sp. Strain VM15C. 1996. Biosci. Biotech. Biochem. 60(7). 1056-1062. (Year: 1996).*

Shimao M et al. The gene pvaB encodes oxidized polyvinyl alcohol hydrolase of Pseudomonas sp. strain VM15C and forms an operon with the polyvinyl alcohol dehydrogenase gene pvaA. 2000. Microbiology. 146, 649-657. (Year: 2000).*

Matsumura et al., "Novel Poly(vinyl alcohol)-Degrading Enzyme and the Degradation Mechanism", Macromolecules, vol. 32, pp. 7753-7761 (1999).

Morita et al., "Purification and Properties of Secondary Alcohol Oxidase from a Strain of Pseudomonas", Agric. Bioi. Chem., vol. 43, pp. 1225-1235 (1979).

Sakai et al., "Purification and Properties of Oxidized Poly(vinyl alcohol)-Degrading Enzyme", Agric. Bioi. Chem., vol. 45, pp. 63-71 (1981).

Sakai et al., "Separation of Secondary Alcohol Oxidase and Oxidized Poly (vinyl alcohol) Hydrolase by Hydrophobic and Dye-ligand Chromatographies", Agric. Bioi. Chem., vol. 47, pp. 153-155 (1983).

Shimao et al., "Cloning and Characterization of the Gene Encoding Pyrroloquinoline Quinone-dependent Poly (vinyl alcohol) Dehydrogenase of Pseudomonas sp. Strain VM15C", Biosci. Biotechnol. Biochem., vol. 60, pp. 1056-1062 (1996).

Yang et al., "Structural Insights into Enzymatic Degradation of Oxidized Polyvinyl Alcohol", Chembiochem, vol. 15, pp. 1882-1886 (2014).

Kawai, F., et al., "Biochemistry of Microbial Polyvinyl Alcohol Degradation", Appl. Microbial. Biotechnol., vol. 84, pp. 227-237 (2009).

(Continued)

Primary Examiner — Paul J Holland
(74) Attorney, Agent, or Firm — BROWDY AND NEIMARK, PLLC

(57) ABSTRACT

The objects of the present invention are to provide a novel PVA-degrading enzyme that the entity of which is revealed at the amino acid sequence level, a process for producing the same, a DNA encoding the enzyme, a recombinant DNA comprising the DNA, and a transformant having the recombinant DNA. The present invention solves the above objects by providing a polyvinyl alcohol-degrading enzyme having the following characteristics (1) to (3), a process for producing the same, a DNA encoding the enzyme, a recombinant DNA comprising the DNA, and a transformant having the recombinant DNA:

(1) having an activity of oxidizing polyvinyl alcohol and forming hydrogen peroxide;
(2) having an activity of hydrolyzing β-diketone; and
(3) exhibiting a molecular weight of 100,000±20,000 in SDS-polyacrylamide gel electrophoresis.

10 Claims, 7 Drawing Sheets

Specification includes a Sequence Listing.

(56) References Cited

OTHER PUBLICATIONS

Shimao, M., et al., "The gene pvaB encodes oxidized polyvinyl alcohol hydrolase of *Pseudomonas* sp. strain VM15C and forms an operon with the polyvinyl alcohol dehydrogenase gene pvaA", Microbiology, vol. 146, pp. 649-657 (2000).

Klomklang, W., et al., "Biochemical and molecular characterization of a periplasmic hydrolase for oxidized polyvinyl alcohol from *Sphingomonas* sp. strain 113P3", Microbiology, vol. 151, pp. 1255-1262 (2005).

Shimao, M., et al., "Properties and Roles of Bacterial Symbionts of Polyvinyl Alcohol-Utilizing Mixed Cultures", Applied and Environmental Microbiology, vol. 46, pp. 605-610 (1983).

DATABASE UniProt [Online] Sep. 5, 2006 (Sep. 5, 2006), "Putative polyvinylalcohol dehydrogenase", XP55722176, retrieved from EBI accession No. UNIPROT:Q0X0G1 Database accession No. Q0X0G1.

DATABASE Geneseq [Online] Jun. 15, 2007 (Jun. 15, 2007), "Pseudomonas oxidative polyvinyl alcohol hydrolase protein sequence", XP55722178, retrieved from EBI accession No. GSP:AAY05495 Database accession No. AAY05495.

DATABASE UniProt [Online] Jan. 20, 2016 (Jan. 20, 2016), "PQQ-like domain from Paraburkholderia caribensis (putative polyvinyl alcohol dehydrogenase activity)", XP55722175, retrieved from EBI accession No. UNIPROT: A0A0P0RNZ5 Database accession No. A0A0P0RNZ5.

DATABASE UniProt [Online] Jan. 20, 2016 (Jan. 20, 2016), "Uncharacterized protein from *Phenylobacterium* sp.", XP55722177, retrieved from EBI accession No. UNIPROT:A0A0Q7DM56 Database accession No. A0A0Q7DM56.

European Search Report EP 18761535, dated Aug. 26, 2020.

Singh RK et al. Protein Engineering Approaches in the Post-Genomic Era. 2017. Current and Peptide Science. 18, 1-11. (Year: 2017).

* cited by examiner

```
PVA-A         1    ------------------------------------------------AENWP    5
PVA-B         1    ------------------------------------------------AENWP    5
PVADH_VM15C 114    PHAIWGPPSASMPLDGPKCKGKIPPIDLSTFDQWNGWGAGITNARFQPNFGLTAADVPRL 173
PVADH_113P3 121    LRAIWGNSVEGTPLDAPQCSSAPTPVDLGAANQWNGWSTEKDNGRFQRKPALDVADIPPL 180

PVA-A         6    MPGKNYENTRATSDTQISTANISTLNVVPRTTDGGITG PTWDGV YYSDFSGY KA R   65
PVA-B         6    MPGKNYENSRATADTQLSTSNISSLNVVRPTADGGITG PTWDGV YYSDFSGY FA R   65
PVADH_VM15C 174    KVKWAFNYPGSKNGQATVVGDRLFVTSMSGAVYALNAR   VNRHDAAAATRSS HV Q  233
PVADH_113P3 181    KLKWAFQYPGSKNGQATVIGDRLFTTSTSGAVYALNAK   VWRK AEGATPTSPVIAA  240

PVA-A        66    VSD VVLWRVRPQTTMLSPSPFVT  VYVAGNNSYVYALNRANGAVRWTTQIETSPNSR 125
PVA-B        66    VND VVLWRVRPQTTMLSPSPFVTDD VYVAGNNSYVYALNRDGAVRWTTQIETSPNSR 125
PVADH_VM15C 234    LPA  PAQYAIFFSDWTKAAVALD  GKQLWKTTIDDQPGVQMTGSPTYHBGRLFVPIS 293
PVADH_113P3 241    LPE  PAKTALFFSDFTKAAVALD  GKQLWKTVVDDQPALQMTGSITVWDGKIYVPIS 300

PVA-A       126    ISSSPIVVGNILTGTGSYQVFLPATPMFPGRVAFLNATTGAILPYSTNMCPSAS CGG I 185
PVA-B       126    ISSSPIVVDNILMIGTGSYQVFIPATPMFRGRVVFLNATTGAILPYSTNMCPSGLCC  I 185
PVADH_VM15C 294    SGNEAPATNDQWECCKFEGALVALDALSGKVLNKTYTTQKEPASFRLNKLGFQMWGPA G 353
PVADH_113P3 301    BGTEAFAQIPTWECCKFBGALVALDAATGKILWKRYTTSQEPR PFKLNKAGRQMWGPS   360

PVA-A       186                                                              244
PVA-B       186                                                              244
PVADH_VM15C 354                                                              413
PVADH_113P3 361                                                              420

PVA-A       245    --------GT PY YDV       V  QRMVG        YR NR DT     NT  291
PVA-B       245    --------GV RY YDV       V  EPRMVG     TYR R DT     TT  291
PVADH_VM15C 414    ----PRAANCPEKVGP AL        HTLQ  RQYII      AV    PQND    MR 469
PVADH_113P3 421    WQKGKEBANCPNP GP FS    LYRK    KEFLL    MY RIYR  PANK    ER 480

PVA-A       292    P  R SA    MQS  YG  RI  TSNTSTIGSGRNDPVPAT  RASALD ATGAPVWIRQ 351
PVA-B       292    P GR S  P  MQS   GV RI  TSNTSTIGGGRNDPVPAT  SALALD ATGTPVWIRQ 351
PVADH_VM15C 470    R SP  EI  SFGM DAENV  BISDVT--TREGGKPGV  LRIRDG DVWAF-SAPR 526
PVADH_113P3 481    QLSL  AL   EPG  AD    V  AGVSDTASQAKDRGK PGSLW  GIFTGEVAWNFLNAPD 540

PVA-A       352    LDAGGFGGVAYANGLMYA  WD  RLRVFNAANGNIVREVQVSPSRGAYVE PTDGFPNGS 411
PVA-B       352    LDAGGFGGVAYANGLMYA  VWD  RMRVFNAANGNIVREVQVSPSRGVYVA PTDGFPNGS 411
PVADH_VM15C 527    TPCRWNNIFCHPAVSQAVTAMP  VYFAGSMDGMFRAFSTDGKVLMEFNT  AAPYKTVAG 586
PVADH_113P3 541    TKCRWNNWWCHGAFSQAI  VIR AT FAGSYDGMFRAFDTATGKIIWDVDTGTKAVTTLSG 600

PVA-A       412     GGPVVYGNRVLMGYGWTW LNI  SLTTMEATV GGASQ VTLASSSDTYVQSGTPTTN 471
PVA-B       412     GSPIVYGNRVLMGYGWTW LNI  GLATMELVS YGETQ VTLASNQDTYVQSGTPTTS 471
PVADH_VM15C 587    KQADGGVMDGAGPTIAGGM  VN   AGRSTQNA   HLRGREGNVLIAPSVDGK------ 639
PVADH_113P3 601     KAPGGVMDGAGPTIAGGM  VK   AGRSSESQ  DLRG DGNILMAFSVDGK------ 654

PVA-A       472    YAYDVNLLARLADAEGLTRASFLQFPLTAVPAGTITSARLRLYGPHDAPTGTGQSVSVWP 531
PVA-B       472    YEANPFLLARLADAEGLTRASFLQFPLTAIPAGTITSARLRLYGRHDAPTGTGCQPVSVWP 531
PVADH_VM15C 639    -----------------------------------------------------------   639
PVADH_113P3 654    -----------------------------------------------------------   654
```

FIG. 7

```
PVA-A      541  PNVTYRNSSTETGVDFYATSSIATATVGITPQYYEWNVTDYVASRRSLGHATFGVAVNSA  600
PVA-B      541  ADVIYNNSDLVTGVSPYLTSPIANALIGITPQYYEWDVTGYVDSRRALGKATFGVAVDYG  600
OPH_VM15C    1  ------------------------------------------------MNQSLGVLR    9
OPH_113P3    0  ---------------------------------------------------------    0

PVA-A      601  HQYR?TLNSADNTA??PELVVIVS-GG?G----SQLP-----GS????AP??MQ???   651
PVA-B      601  HLYR?TFNSADNA??PELVV?VSTCK?SEPDPELPGSMEGS?????PR???MQ???   660
OPH_VM15C   10  LTR??TALALASV?SGCSSTG?DETA??FAAANPAATEPVRW????EVK??????    69
OPH_113P3    1  ----?PXPVVKSES??FPCYI?GCLAMVAATLSSTAQA?SEWA????PF???T???    56

PVA-A      652  N?VA?????NV?A??S??P??GL???E?TD??LG-A??G???????N?DGF?YI?VP?   709
PVA-B      661  N?VA?????KNV?A??ST?????L???????????????????????TRI???????   718
OPH_VM15C   70  K??????IVYPAK??G?A??VM?????N?KT?VA?S?ANS??ADM?Y?V?P?A      129
OPH_113P3   57  DGK?????VVP?KDSAGGA?W?PMV??V???W??NVP?S??N???AEH??WI?EVQ   116

PVA-A      710  ?A??DP??AGTSVG????QAG?G?????WNP?????GV?FA?????????????AV?   769
PVA-B      719  ??QDP??SGTSVG???????PA??????????????????????????????SVA?   778
OPH_VM15C  130  C??QDPN-----IPS?R??GPS??R?NN??P?ADRS???????????????VAM?Q   184
OPH_113P3  117  C??QDPN-----LCA?A??VGPD??W?NP???GRPQ?S??GKY?D?G?DVE?KM?K   171

PVA-A      770  ?VAASYPV??STE?Y????GTS??????RALLE?S?WAGC?????SSEN????????AY?GAD  829
PVA-B      779  ?AFRFPV??K??Y????????P?T?????ALB??????????????SS?BN??????AY?GPD  838
OPH_VM15C  185  ?VGTKYKL??RK?PLGGIS??????????RALLP???WAGG?????SSEN????????PLS---  241
OPH_113P3  172  ?VGTKWKL??RK?PLGGIS??????????RALLB???WAGG?????SSEN??????????TV?---  228

PVA-A      830  ??AA??????NN???QCHV???????ATQ?????SAM?????------?STL???     884
PVA-B      839  ??AA?????IDE???QCRV???????STL?????????????---?VT??????       894
OPH_VM15C  242  -?DDA?????AAA???K?CRVGP???AKV???????GGG????KN?TRPLG?R??????   300
OPH_113P3  229  -?QET?????NAAA????QCRV????SKL???????????ESHG???W??DPPL?---???   284

PVA-A      885  ?RP??????ASP???GL?????VHVACS?????G?DP???????AT?????ASHPK??TPASS??  944
PVA-B      895  ?KP?????A????????????VHVACG????????????TI?A?????????ASHPK??TPASA??  954
OPH_VM15C  301  ?RP??????S??????????VVHVACS???????????TQE??A????????ASHPK??SDPRE?   360
OPH_113P3  285  ?RP???????SN??PSS?S?VVHVACS?ATG?????????N?MAL?????ASHPK??SSPKT??   344

PVA-A      945  ?PP???V????RV???????GGT-----------------------------       965
PVA-B      955  ?PP?????L????PYI???ERACSVDGDGDIDRMDIAVITAARNQFASGPTDLFDVDRSG  1014
OPH_VM15C  361  ?TQ????V???HVGPF?GL------------------------------      379
OPH_113P3  345  ?TAP???GV?KI??PT????K-----------------------------      364

PVA-A      966  ----------------------    966
PVA-B     1015  VIDVNDARACTLRCDRPNCAVQ   1036
OPH_VM15C  379  ----------------------    379
OPH_113P3  364  ----------------------    364
```

FIG. 8

SEQUENCE LISTING

```
<160> NUMBER OF SEQ ID NOS: 16

<210> SEQ ID NO 1
<211> LENGTH: 13
<212> TYPE: PRT
<213> ORGANISM: Pseudomonas sp.

<400> SEQUENCE: 1

Ala Glu Asn Trp Pro Met Phe Gly Lys Asn Tyr Glu Asn
1               5                   10

<210> SEQ ID NO 2
<211> LENGTH: 966
<212> TYPE: PRT
<213> ORGANISM: Pseudomonas sp.

<400> SEQUENCE: 2

Ala Glu Asn Trp Pro Met Phe Gly Lys Asn Tyr Glu Asn Thr Arg Ala
1               5                   10                  15

Thr Ser Asp Thr Gln Ile Ser Thr Ala Asn Ile Ser Thr Leu Asn Val
            20                  25                  30

Val Arg Arg Thr Thr Asp Gly Gly Ile Thr Gly Thr Pro Thr Val Val
        35                  40                  45

Asp Gly Val Ala Tyr Tyr Ser Asp Phe Ser Gly Tyr Val Lys Ala Val
    50                  55                  60

Arg Val Ser Asp Gly Val Val Leu Trp Arg Val Arg Pro Gln Thr Thr
65                  70                  75                  80

Met Leu Ser Pro Ser Pro Phe Val Thr Ala Asp Thr Val Tyr Val Ala
                85                  90                  95

Gly Asn Asn Ser Tyr Val Tyr Ala Leu Asn Arg Ala Asn Gly Ala Val
            100                 105                 110

Arg Trp Thr Thr Gln Ile Glu Thr Ser Pro Asn Ser Arg Ile Ser Ser
        115                 120                 125

Ser Pro Ile Val Val Gly Asn Ile Leu Ile Ile Gly Thr Gly Ser Tyr
    130                 135                 140

Gln Val Phe Leu Pro Ala Thr Pro Met Phe Arg Gly Arg Val Ala Phe
145                 150                 155                 160

Leu Asn Ala Thr Thr Gly Ala Ile Leu Pro Tyr Ser Thr Asn Met Cys
                165                 170                 175

Pro Ser Ala Ser Cys Gly Gly Ile Ser Val Trp Ser Thr Ala Ala
            180                 185                 190

Ile Asp Glu Ser Thr Arg Thr Gly Tyr Ile Gly Thr Gly Gln Ala Tyr
        195                 200                 205

Arg Asp Pro Ala Gly Pro Tyr Ser Asp Ala Leu Val Ala Phe Asn Ile
```

```
              210                 215                 220
Asp Thr Gly Ala Ile Arg Trp Ala Arg Gln Phe Leu Ala Asn Asp Val
225                 230                 235                 240

Tyr Gln Leu Gly Gly Thr Leu Arg Tyr Asp Tyr Asp Val Gly Ala Ala
                    245                 250                 255

Pro Asn Leu Phe Val Ala Asn Gly Gln Arg Met Val Gly Val Gly Gly
                260                 265                 270

Lys Asp Gly Thr Tyr Arg Ala Phe Asn Arg Asp Thr Gly Ala Pro Ile
            275                 280                 285

Trp Asn Thr Pro Val Gly Arg Gly Ser Ala Ile Gly Gly Val Met Gln
        290                 295                 300

Ser Thr Ala Tyr Gly Asp Gly Arg Ile Tyr Val Thr Ser Asn Thr Ser
305                 310                 315                 320

Thr Ile Gly Ser Gly Arg Asn Asp Pro Val Pro Ala Thr Ala Glu Ala
                    325                 330                 335

Ser Ala Leu Asp Ala Ala Thr Gly Ala Pro Val Trp Ile Arg Gln Leu
                340                 345                 350

Asp Ala Gly Gly Phe Gly Gly Val Ala Tyr Ala Asn Gly Leu Met Tyr
            355                 360                 365

Ala Ser Thr Trp Asp Gly Arg Leu Arg Val Phe Asn Ala Ala Asn Gly
        370                 375                 380

Asn Ile Val Arg Glu Val Gln Val Ser Pro Ser Arg Gly Ala Tyr Val
385                 390                 395                 400

Pro Ala Pro Thr Asp Gly Phe Pro Asn Gly Ser Ala Gly Gly Pro Val
                    405                 410                 415

Val Tyr Gly Asn Arg Val Leu Met Gly Tyr Gly Trp Thr Trp Val Leu
                420                 425                 430

Asn Ile Asn Gly Gly Leu Thr Thr Met Glu Ala Thr Val Gly Gly Gly
            435                 440                 445

Ala Ser Gln Thr Val Thr Leu Ala Ser Ser Ser Asp Thr Tyr Val Gln
        450                 455                 460

Ser Gly Thr Pro Thr Thr Asn Tyr Ala Tyr Asp Val Asn Leu Leu Ala
465                 470                 475                 480

Arg Leu Ala Asp Ala Glu Gly Leu Thr Arg Ala Ser Phe Leu Gln Phe
                    485                 490                 495

Pro Leu Thr Ala Val Pro Ala Gly Thr Ile Thr Ser Ala Arg Leu Arg
                500                 505                 510

Leu Tyr Gly Arg His Asp Ala Pro Thr Gly Thr Gly Gln Ser Val Ser
            515                 520                 525

Val Trp Pro Gly Thr Lys Thr Thr Trp Ser Gly Pro Asn Val Thr
        530                 535                 540

Tyr Asn Asn Ser Ser Thr Glu Thr Gly Val Asp Phe Tyr Ala Thr Ser
545                 550                 555                 560

Ser Ile Ala Thr Ala Thr Val Gly Ile Thr Pro Gln Tyr Tyr Glu Trp
                    565                 570                 575

Asn Val Thr Asp Tyr Val Ala Ser Arg Arg Ser Leu Gly His Ala Thr
                580                 585                 590

Phe Gly Val Ala Val Asn Ser Ala His Gln Tyr Arg Val Thr Leu Asn
            595                 600                 605

Ser Ala Asp Asn Thr Ala Asn Arg Pro Glu Leu Val Val Thr Val Ser
        610                 615                 620

Gly Gly Thr Gly Ser Gln Leu Pro Gly Ser Cys Pro Ser Gly Phe Thr
625                 630                 635                 640
```

Ala Arg Ala Gly Val Asn Gln Gly Phe Met His Asn Gly Val Ala Arg
            645                 650                 655

Gly Phe Val Leu Asn Val Pro Ala Asn Val Ser Thr Pro Arg Pro Val
            660                 665                 670

Phe Val Ser Leu Thr Gly Ser Val Glu Ser Thr Asn Glu Asn Leu Gly
            675                 680                 685

Ala Arg Gly Gly Ala Gly Ala Leu Asn Asn Asp Gly Phe Leu Val Ile
            690                 695                 700

Gly Pro Val Arg Arg Cys Ala Gly Gln Asp Pro Asn Gly Ala Gly Thr
705                 710                 715                 720

Ser Val Asn Gly Gly Thr Cys Asn Gln Ala Gly Thr Gly Gly Trp Asn
                725                 730                 735

Trp Asn Pro Trp Asn Glu Gly Arg Val Phe Ala Ala Ala Gly Asp Pro
            740                 745                 750

Trp Lys Thr Ala Glu Gly Pro Asp Ser Gln Phe Leu Glu Ala Val Val
            755                 760                 765

Arg Cys Val Ala Ala Ser Tyr Pro Val Asp Ser Thr Arg Met Tyr Leu
            770                 775                 780

Gly Gly Ile Ser Ser Gly Ala Thr Met Thr His Arg Ala Leu Leu Phe
785                 790                 795                 800

Asn Ser Asp Phe Trp Ala Gly Leu Pro Leu Ser Gly Glu Trp Tyr
                805                 810                 815

Val Ser Gln Asp Asn Gly Thr Ala Tyr Pro Gly Ala Asp Glu Phe Ala
                820                 825                 830

Ala Arg Arg Gln Ala Val Ile Asn Asn Pro Thr Lys Ile Phe Gln Gly
                835                 840                 845

Arg Val Gly Pro Leu Pro Leu Pro Ala Thr Gln Ser Pro Met Ile Val
            850                 855                 860

Ile Ser Met Trp Gly Gly Ala Asn Asp Ile Trp Tyr Cys Gly Ser Thr
865                 870                 875                 880

Leu Cys Ala Asp Tyr Arg Pro Ser Thr Gln Ala Ala Ser Asn Tyr Phe
                885                 890                 895

Ser Ala Leu Pro Asn Val Val His Val Ala Cys Ser Ser His Gly
            900                 905                 910

His Gln Trp Pro Thr Gln Asn Arg Ala Ala Phe Asn Thr Trp Ala Ala
            915                 920                 925

Thr Thr Leu Ala Ser His Pro Lys Gly Thr Pro Ala Ser Ser Phe Val
            930                 935                 940

Leu Pro Pro Pro Ala Gly Tyr Ser Cys Arg Val Gly Arg Tyr Thr
945                 950                 955                 960

Asp His Tyr Ser Gly Thr
                965

<210> SEQ ID NO 3
<211> LENGTH: 1036
<212> TYPE: PRT
<213> ORGANISM: Pseudomonas sp.

<400> SEQUENCE: 3

Ala Glu Asn Trp Pro Met Phe Gly Lys Asn Tyr Glu Asn Ser Arg Ala
1               5                   10                  15

Thr Ala Asp Thr Gln Leu Ser Thr Ser Asn Ile Ser Ser Leu Asn Val
            20                  25                  30

Val Arg Arg Thr Ala Asp Gly Gly Ile Thr Gly Thr Pro Thr Val Val

```
            35                  40                  45
Asp Gly Val Ala Tyr Tyr Ser Asp Phe Ser Gly Tyr Val Lys Ala Val
            50                  55                  60
Arg Val Asn Asp Gly Ala Val Leu Trp Arg Val Arg Pro Gln Thr Thr
 65                  70                  75                  80
Met Leu Ser Pro Ser Pro Phe Val Thr Asp Thr Val Tyr Val Ala
                85                  90                  95
Gly Asn Asn Ser Tyr Val Tyr Ala Leu Asn Arg Leu Asp Gly Ala Val
                100                 105                 110
Arg Trp Thr Thr Gln Ile Glu Thr Ser Pro Asn Ser Arg Ile Ser Ser
                115                 120                 125
Ser Pro Ile Val Val Asp Asn Ile Leu Met Ile Gly Thr Gly Ser Tyr
                130                 135                 140
Gln Val Phe Ile Pro Ala Thr Pro Met Phe Arg Gly Arg Val Val Phe
145                 150                 155                 160
Leu Asn Ala Thr Thr Gly Ala Ile Leu Pro Tyr Ser Thr Asn Met Cys
                165                 170                 175
Pro Glu Gly Leu Cys Gly Gly Ile Ser Val Trp Ser Thr Ala Ala
                180                 185                 190
Val Asp Val Ser Thr Arg Thr Gly Tyr Ile Gly Thr Gly Gln Ala Tyr
                195                 200                 205
Arg Asp Pro Ala Gly Pro Tyr Ser Asp Ser Leu Val Ala Phe Asp Ile
                210                 215                 220
Asp Thr Gly Ala Ile Arg Trp Ser Gln Gln Phe Leu Ala Asn Asp Val
225                 230                 235                 240
Tyr Gln Leu Gly Gly Val Leu Arg Tyr Asp Tyr Asp Val Gly Ala Ala
                245                 250                 255
Pro Asn Leu Phe Val Ala Asp Glu Arg Arg Met Val Gly Val Gly Gly
                260                 265                 270
Lys Asp Gly Thr Tyr Arg Ala Phe Asp Arg Asp Thr Gly Ala Pro Ile
                275                 280                 285
Trp Thr Thr Pro Val Gly Arg Gly Ser Pro Ile Gly Gly Val Met Gln
                290                 295                 300
Ser Thr Ala Tyr Gly Asp Gly Arg Ile Tyr Val Thr Ser Asn Thr Ser
305                 310                 315                 320
Thr Ile Gly Gly Arg Asn Asp Pro Val Pro Ala Thr Ala Glu Ala
                325                 330                 335
Leu Ala Leu Asp Ala Ala Thr Gly Thr Pro Val Trp Ile Arg Gln Leu
                340                 345                 350
Asp Ala Gly Gly Phe Gly Gly Val Ala Tyr Ala Asn Gly Leu Met Tyr
                355                 360                 365
Ala Ser Val Trp Asp Gly Arg Met Arg Val Phe Asn Ala Ala Asn Gly
                370                 375                 380
Asn Ile Val Lys Glu Val Gln Val Ser Pro Ser Arg Gly Val Tyr Val
385                 390                 395                 400
Ala Ala Pro Thr Asp Gly Phe Pro Asn Gly Ser Ala Gly Gly Pro Ile
                405                 410                 415
Val Tyr Gly Asn Arg Val Leu Met Gly Tyr Gly Trp Thr Trp Val Leu
                420                 425                 430
Asn Ile Ser Gly Gly Leu Ala Thr Met Glu Leu Val Ser Gly Gly Gly
                435                 440                 445
Glu Thr Gln Thr Val Thr Leu Ala Ser Asn Gln Asp Thr Tyr Val Gln
450                 455                 460
```

```
Ser Gly Thr Pro Thr Thr Ser Tyr Asn Ala Asn Glu Phe Leu Leu Ala
465                 470                 475                 480

Arg Leu Ala Asp Ala Glu Gly Leu Thr Arg Ala Ser Phe Leu Gln Phe
            485                 490                 495

Pro Leu Thr Ala Ile Pro Ala Gly Thr Ile Thr Ser Ala Arg Leu Arg
                500                 505                 510

Leu Tyr Gly Arg His Asp Ala Pro Thr Gly Thr Gly Gln Pro Val Ser
        515                 520                 525

Val Trp Pro Gly Thr Phe Thr Thr Pro Trp Asn Gly Ala Asp Val Ile
        530                 535                 540

Tyr Asn Asn Ser Asp Leu Val Thr Gly Val Asn Phe Tyr Leu Thr Ser
545                 550                 555                 560

Pro Ile Ala Asn Ala Leu Ile Gly Ile Thr Pro Gln Tyr Tyr Glu Trp
                565                 570                 575

Asp Val Thr Gly Tyr Val Asp Ser Arg Arg Ala Leu Gly His Ala Thr
                580                 585                 590

Phe Gly Val Ala Val Asp Tyr Gly His Leu Tyr Arg Val Thr Phe Asn
        595                 600                 605

Ser Ala Asp Asn Ala Ala Asn Arg Pro Glu Leu Val Val Ala Val Ser
610                 615                 620

Thr Gly Gly Thr Ser Glu Pro Asp Pro Glu Leu Pro Pro Gly Ser Met
625                 630                 635                 640

Glu Gly Ser Cys Pro Ala Gly Phe Thr Pro Arg Ala Gly Val Asn Gln
                645                 650                 655

Gly Phe Ile His Asn Gly Val Ala Arg Gly Phe Val Leu Asn Val Pro
                660                 665                 670

Ala Asn Val Ser Thr Pro Arg Pro Met Phe Val Ser Leu Thr Gly Ser
                675                 680                 685

Val Glu Ser Thr Asn Glu Asn Leu Gly Pro Arg Gly Gly Ala Gly Ala
        690                 695                 700

Leu Thr Asn Asp Gly Phe Leu Val Ile Gly Pro Val Arg Arg Cys Ala
705                 710                 715                 720

Gly Gln Asp Pro Asn Gly Ser Gly Thr Ser Val Gly Gly Gly Thr Cys
                725                 730                 735

Asn Gln Pro Gly Thr Gly Gly Trp Asn Trp Asn Pro Trp Asn Glu Gly
                740                 745                 750

Arg Ala Phe Gly Ala Ala Gly Asp Gln Trp Lys Thr Ala Glu Gly Pro
            755                 760                 765

Asp Ser Glu Phe Leu Glu Ser Val Ala Arg Cys Val Ala Lys Arg Phe
        770                 775                 780

Pro Val Asp Ser Lys Arg Met Tyr Leu Gly Gly Ile Ser Ser Gly Gly
785                 790                 795                 800

Thr Leu Thr Asn Arg Ala Leu Leu Phe Asn Ser Asp Phe Trp Ala Gly
                805                 810                 815

Gly Leu Pro Ile Ser Gly Glu Trp Tyr Val Thr Arg Asp Asp Gly Thr
                820                 825                 830

Ala Tyr Pro Gly Pro Asp Glu Phe Ala Ala Arg Arg Gln Ala Val Ile
                835                 840                 845

Asp Asp Pro Thr Lys Ile Phe Gln Gly Arg Val Gly Pro Leu Pro Leu
                850                 855                 860

Arg Ser Thr Leu Asp Pro Met Ile Val Ile Thr Val Trp Gly Gly Thr
865                 870                 875                 880
```

```
-continued

Asn Asp Val Trp Ser Cys Asp Gly Val Thr Leu Cys Ala Asp Tyr Arg
                885                 890                 895

Pro Ser Thr Gln Val Ala Ser Asn Tyr Phe Ser Ala Gln Pro Asn Val
            900                 905                 910

Val His Val Ala Cys Ser Ser His Gly His Gln Trp Pro Thr Ile
        915                 920                 925

Asn Arg Ala Ala Phe Asn Thr Trp Ala Ala Thr Thr Leu Ala Ser His
        930                 935                 940

Pro Lys Gly Thr Pro Ala Ser Ala Phe Val Leu Pro Pro Pro Ala
945                 950                 955                 960

Gly Tyr Thr Cys Arg Ile Gly Pro Tyr Ile Asp His Tyr Glu Arg Ala
                965                 970                 975

Cys Ser Val Asp Gly Asp Gly Asp Ile Asp Arg Asn Asp Ile Ala Val
                980                 985                 990

Ile Thr Ala Ala Arg Asn Gln Pro Ala Ser Gly Pro Thr Asp Leu Arg
            995                 1000                1005

Asp Val Asp Arg Ser Gly Val Ile Asp Val Asn Asp Ala Arg Ala
    1010                1015                1020

Cys Thr Leu Arg Cys Asp Arg Pro Asn Cys Ala Val Gln
    1025                1030                1035

<210> SEQ ID NO 4
<211> LENGTH: 2976
<212> TYPE: DNA
<213> ORGANISM: Pseudomonas sp.
<220> FEATURE:
<221> NAME/KEY: CDS
<222> LOCATION: (1)..(2976)

<400> SEQUENCE: 4 atg aaa cag ttg agg aca ctg gca tgt att gcc gcg gtg ggt ctc agt      48
Met Lys Gln Leu Arg Thr Leu Ala Cys Ile Ala Ala Val Gly Leu Ser
1               5                   10                  15 gtg tcc ggc atg atg agt ccg gcc acg gct gct gag aac tgg ccg atg      96
Val Ser Gly Met Met Ser Pro Ala Thr Ala Ala Glu Asn Trp Pro Met
            20                  25                  30 ttc ggc aag aat tat gag aac aca cgc gcc acc agc gac aca cag atc     144
Phe Gly Lys Asn Tyr Glu Asn Thr Arg Ala Thr Ser Asp Thr Gln Ile
        35                  40                  45 tcg acc gcc aac att tcg acg ctc aac gtc gta cgt cgt acg acc gat     192
Ser Thr Ala Asn Ile Ser Thr Leu Asn Val Val Arg Arg Thr Thr Asp
    50                  55                  60 ggc ggc atc act ggc aca ccg acc gtg gtc gac ggt gtg gct tac tac     240
Gly Gly Ile Thr Gly Thr Pro Thr Val Val Asp Gly Val Ala Tyr Tyr
65                  70                  75                  80 tct gac ttc tcc ggt tat gtg aag gcg gtg cgc gtc agc gat ggc gtc     288
Ser Asp Phe Ser Gly Tyr Val Lys Ala Val Arg Val Ser Asp Gly Val
                85                  90                  95 gtg ttg tgg cgc gtg cgt ccg cag acg acg atg ctc tcg cca tcg cca     336
Val Leu Trp Arg Val Arg Pro Gln Thr Thr Met Leu Ser Pro Ser Pro
            100                 105                 110 ttc gtg acg gcc gac acg gtc tat gtc gcc ggc aac aac tcg tac gtg     384
Phe Val Thr Ala Asp Thr Val Tyr Val Ala Gly Asn Asn Ser Tyr Val
        115                 120                 125 tat gcg ctc aac cgc gcg aac ggt gca gtt cgc tgg acg acg cag atc     432
Tyr Ala Leu Asn Arg Ala Asn Gly Ala Val Arg Trp Thr Thr Gln Ile
    130                 135                 140 gag acg tcg ccg aac agc cgt atc tcc tcc tcg ccg atc gtg gtc ggc     480
Glu Thr Ser Pro Asn Ser Arg Ile Ser Ser Ser Pro Ile Val Val Gly
```

|  |  |
|---|---|
| aac atc ctg atc atc ggt acg ggt tcg tat cag gtg ttc ctt ccc gca<br>Asn Ile Leu Ile Ile Gly Thr Gly Ser Tyr Gln Val Phe Leu Pro Ala<br>                  165                170               175 | 528 |
| acg ccg atg ttc cgc ggt cgg gtc gca ttc ctg aat gcg acg acg ggc<br>Thr Pro Met Phe Arg Gly Arg Val Ala Phe Leu Asn Ala Thr Thr Gly<br>        180                  185               190 | 576 |
| gcg atc ctg ccg tac agc acc aac atg tgt ccg agc gct tcc tgc ggc<br>Ala Ile Leu Pro Tyr Ser Thr Asn Met Cys Pro Ser Ala Ser Cys Gly<br>                195                200               205 | 624 |
| ggc ggc atc tcg gtg tgg tcg acc gcg gcc att gac gag tcc acg cgc<br>Gly Gly Ile Ser Val Trp Ser Thr Ala Ala Ile Asp Glu Ser Thr Arg<br>        210                  215               220 | 672 |
| acc ggc tac atc ggc acc gga cag gct tat cgc gat cct gcg ggc ccg<br>Thr Gly Tyr Ile Gly Thr Gly Gln Ala Tyr Arg Asp Pro Ala Gly Pro<br>225                  230                235               240 | 720 |
| tat tcc gat gcg ctc gtg gcg ttc aac atc gac acg ggt gcg att cgc<br>Tyr Ser Asp Ala Leu Val Ala Phe Asn Ile Asp Thr Gly Ala Ile Arg<br>                245                250               255 | 768 |
| tgg gcc cgg cag ttc ctg gcc aac gac gtg tat cag ctg ggc ggc acg<br>Trp Ala Arg Gln Phe Leu Ala Asn Asp Val Tyr Gln Leu Gly Gly Thr<br>        260                  265               270 | 816 |
| ctg cgc tat gac tac gac gtg ggc gcg gcg ccg aat ctg ttc gtt gcg<br>Leu Arg Tyr Asp Tyr Asp Val Gly Ala Ala Pro Asn Leu Phe Val Ala<br>                275                280               285 | 864 |
| aac ggg cag cgc atg gta ggc gtc ggc ggc aag gac gga acc tac agg<br>Asn Gly Gln Arg Met Val Gly Val Gly Gly Lys Asp Gly Thr Tyr Arg<br>        290                  295               300 | 912 |
| gcg ttc aat cgc gat acc ggt gcg ccg atc tgg aat acc ccg gtg ggg<br>Ala Phe Asn Arg Asp Thr Gly Ala Pro Ile Trp Asn Thr Pro Val Gly<br>305                  310                315               320 | 960 |
| cgc ggc agc gcc att ggc ggg gtg atg cag tca acc gcc tat ggc gac<br>Arg Gly Ser Ala Ile Gly Gly Val Met Gln Ser Thr Ala Tyr Gly Asp<br>                325                330               335 | 1008 |
| ggc cgc atc tac gtc acc agc aat acg tcg acc atc ggt tcg ggt cgc<br>Gly Arg Ile Tyr Val Thr Ser Asn Thr Ser Thr Ile Gly Ser Gly Arg<br>                340                345               350 | 1056 |
| aat gat ccc gtg ccc gca acg gcc gaa gca tcg gcg ctc gat gct gcg<br>Asn Asp Pro Val Pro Ala Thr Ala Glu Ala Ser Ala Leu Asp Ala Ala<br>                355                360               365 | 1104 |
| acg ggt gcg ccc gtg tgg atc cga cag ctc gat gcc ggc ggc ttt ggc<br>Thr Gly Ala Pro Val Trp Ile Arg Gln Leu Asp Ala Gly Gly Phe Gly<br>        370                  375               380 | 1152 |
| ggc gtc gcc tac gcg aac gga ctc atg tac gcc tcg acc tgg gat ggc<br>Gly Val Ala Tyr Ala Asn Gly Leu Met Tyr Ala Ser Thr Trp Asp Gly<br>385                  390                395               400 | 1200 |
| cgg ctg cgc gtc ttc aat gcc gcc aac ggc aat atc gtc agg gaa gtg<br>Arg Leu Arg Val Phe Asn Ala Ala Asn Gly Asn Ile Val Arg Glu Val<br>                405                410               415 | 1248 |
| cag gtc tcg cca tcg cgc ggc gcg tat gtg cca gcg ccg acg gac gga<br>Gln Val Ser Pro Ser Arg Gly Ala Tyr Val Pro Ala Pro Thr Asp Gly<br>        420                  425               430 | 1296 |
| ttc ccg aat ggc tct gca ggc ggt ccg gtg gtc tac ggc aat cgc gtg<br>Phe Pro Asn Gly Ser Ala Gly Gly Pro Val Val Tyr Gly Asn Arg Val<br>                435                440               445 | 1344 |
| ctg atg ggc tat ggc tgg acg tgg gtg ctc aac atc aac ggc ggc ctg<br>Leu Met Gly Tyr Gly Trp Thr Trp Val Leu Asn Ile Asn Gly Gly Leu<br>        450                  455               460 | 1392 |
| acg acg atg gag gcg act gtc ggt ggc ggt gct tcg cag acg gtc acg | 1440 |

```
Thr Thr Met Glu Ala Thr Val Gly Gly Gly Ala Ser Gln Thr Val Thr
465                 470                 475                 480 ctc gca tcg agt tcc gac acg tat gtt cag agc gga acg ccg acg acc      1488
Leu Ala Ser Ser Ser Asp Thr Tyr Val Gln Ser Gly Thr Pro Thr Thr
                485                 490                 495 aac tac gcc tat gac gtg aat ctg ctg gcg cgg ctg gcg gac gcg gag      1536
Asn Tyr Ala Tyr Asp Val Asn Leu Leu Ala Arg Leu Ala Asp Ala Glu
            500                 505                 510 ggc ctc acc cgg gca tca ttc ctg cag ttc ccg ctg acg gcc gtt cct      1584
Gly Leu Thr Arg Ala Ser Phe Leu Gln Phe Pro Leu Thr Ala Val Pro
        515                 520                 525 gcc ggg acg atc acc tcg gcg cgg cta cgg ctc tat ggc cgt cac gat      1632
Ala Gly Thr Ile Thr Ser Ala Arg Leu Arg Leu Tyr Gly Arg His Asp
    530                 535                 540 gcg ccg acc ggc acg gga caa tcc gtc tcc gtc tgg cct ggc acc aag      1680
Ala Pro Thr Gly Thr Gly Gln Ser Val Ser Val Trp Pro Gly Thr Lys
545                 550                 555                 560 acc acg acg tgg agc gga cct aac gtc acc tac aac aat tcg agc acg      1728
Thr Thr Thr Trp Ser Gly Pro Asn Val Thr Tyr Asn Asn Ser Ser Thr
                565                 570                 575 gag acg ggc gtc gac ttt tac gcc acc agc tcc att gcc act gca acc      1776
Glu Thr Gly Val Asp Phe Tyr Ala Thr Ser Ser Ile Ala Thr Ala Thr
            580                 585                 590 gtg ggc atc acg ccg cag tac tac gaa tgg aat gtc acg gac tat gtg      1824
Val Gly Ile Thr Pro Gln Tyr Tyr Glu Trp Asn Val Thr Asp Tyr Val
        595                 600                 605 gct tcg cgt cga tcg ctg ggc cat gcg aca ttc ggt gtt gcc gtg aac      1872
Ala Ser Arg Arg Ser Leu Gly His Ala Thr Phe Gly Val Ala Val Asn
    610                 615                 620 tcg gcg cat cag tat cgc gtc acg ctc aac tcc gca gac aac acg gcg      1920
Ser Ala His Gln Tyr Arg Val Thr Leu Asn Ser Ala Asp Asn Thr Ala
625                 630                 635                 640 aat cgg ccg gaa ctc gtc gtg acg gtg agt ggc ggc acc ggc agt cag      1968
Asn Arg Pro Glu Leu Val Val Thr Val Ser Gly Gly Thr Gly Ser Gln
                645                 650                 655 ctg ccg ggc agc tgc ccg agc gga ttc acg gcg cgt gcc ggt gtg aat      2016
Leu Pro Gly Ser Cys Pro Ser Gly Phe Thr Ala Arg Ala Gly Val Asn
            660                 665                 670 cag ggc ttc atg cac aac ggc gta gcc cgc ggg ttc gtg ctg aat gtg      2064
Gln Gly Phe Met His Asn Gly Val Ala Arg Gly Phe Val Leu Asn Val
        675                 680                 685 ccg gcc aat gtc tca acg ccg cgc ccc gtg ttc gtc tcg ctc acc ggc      2112
Pro Ala Asn Val Ser Thr Pro Arg Pro Val Phe Val Ser Leu Thr Gly
    690                 695                 700 tcg gtc gag tcg acg aac gag aat ctc gga gcc cgc ggt ggc gcc ggt      2160
Ser Val Glu Ser Thr Asn Glu Asn Leu Gly Ala Arg Gly Gly Ala Gly
705                 710                 715                 720 gcg ctc aac aac gat ggc ttc ctg gtc atc ggc ccg gtg cgt cgc tgc      2208
Ala Leu Asn Asn Asp Gly Phe Leu Val Ile Gly Pro Val Arg Arg Cys
                725                 730                 735 gcc ggt cag gat ccg aac ggc gcc ggg acc agt gtc aac ggc gga acc      2256
Ala Gly Gln Asp Pro Asn Gly Ala Gly Thr Ser Val Asn Gly Gly Thr
            740                 745                 750 tgc aat cag gcg ggt acg ggc ggc tgg aac tgg aat ccg tgg aat gaa      2304
Cys Asn Gln Ala Gly Thr Gly Gly Trp Asn Trp Asn Pro Trp Asn Glu
        755                 760                 765 ggt cgc gta ttc gct gcg gcc gga gat ccc tgg aag acg gcc gaa ggt      2352
Gly Arg Val Phe Ala Ala Ala Gly Asp Pro Trp Lys Thr Ala Glu Gly
    770                 775                 780
```

| | |
|---|---|
| ccg gac tcg cag ttc ctg gaa gcg gtg gtt cgc tgt gta gcg gca agc<br>Pro Asp Ser Gln Phe Leu Glu Ala Val Val Arg Cys Val Ala Ala Ser<br>785                  790                  795                  800 | 2400 |
| tat ccg gtc gac tcg acg cgc atg tat ctc ggc ggc att tct tcc ggc<br>Tyr Pro Val Asp Ser Thr Arg Met Tyr Leu Gly Gly Ile Ser Ser Gly<br>              805                  810                  815 | 2448 |
| gcg acc atg acg cac cgg gcg ctg ctg ttc aac tcg gac ttc tgg gcg<br>Ala Thr Met Thr His Arg Ala Leu Leu Phe Asn Ser Asp Phe Trp Ala<br>820                  825                  830 | 2496 |
| ggc ggc ctg ccg ctc tcg ggc gag tgg tac gtc agc cag gac aat ggc<br>Gly Gly Leu Pro Leu Ser Gly Glu Trp Tyr Val Ser Gln Asp Asn Gly<br>              835                  840                  845 | 2544 |
| acg gcc tat ccg ggc gcg gat gag ttc gct gcg cgg cgt cag gca gtg<br>Thr Ala Tyr Pro Gly Ala Asp Glu Phe Ala Ala Arg Arg Gln Ala Val<br>850                  855                  860 | 2592 |
| atc aac aat ccg acc aag atc ttc cag ggt cgg gtg ggt ccg ctg ccg<br>Ile Asn Asn Pro Thr Lys Ile Phe Gln Gly Arg Val Gly Pro Leu Pro<br>865                  870                  875                  880 | 2640 |
| ctg ccg gca acg cag agt ccg atg atc gtc atc tcg atg tgg ggt ggc<br>Leu Pro Ala Thr Gln Ser Pro Met Ile Val Ile Ser Met Trp Gly Gly<br>              885                  890                  895 | 2688 |
| gcg aac gac atc tgg tac tgc ggc agc acc ctg tgt gcc gac tat cgg<br>Ala Asn Asp Ile Trp Tyr Cys Gly Ser Thr Leu Cys Ala Asp Tyr Arg<br>900                  905                  910 | 2736 |
| ccg agc acg cag gcg gcg tcc aac tac ttc agt gcc ctg ccg aac gtc<br>Pro Ser Thr Gln Ala Ala Ser Asn Tyr Phe Ser Ala Leu Pro Asn Val<br>              915                  920                  925 | 2784 |
| gtg cac gtc gcc tgt tcg tcg agc cac ggt cac cag tgg ccg aca cag<br>Val His Val Ala Cys Ser Ser Ser His Gly His Gln Trp Pro Thr Gln<br>930                  935                  940 | 2832 |
| aat cgc gcc gcg ttc aac acg tgg gcg gcc acg acg ctg gca tcg cat<br>Asn Arg Ala Ala Phe Asn Thr Trp Ala Ala Thr Thr Leu Ala Ser His<br>945                  950                  955                  960 | 2880 |
| ccg aag gga acg ccg gct tcg tcg ttc gtt ctg ccg ccg ccg gcg<br>Pro Lys Gly Thr Pro Ala Ser Ser Phe Val Leu Pro Pro Pro Ala<br>              965                  970                  975 | 2928 |
| ggt tac agc tgc cgg gtc ggc cgc tac acg gat cac tac agc gga acg<br>Gly Tyr Ser Cys Arg Val Gly Arg Tyr Thr Asp His Tyr Ser Gly Thr<br>980                  985                  990 | 2976 |

```
<210> SEQ ID NO 5
<211> LENGTH: 3186
<212> TYPE: DNA
<213> ORGANISM: Pseudomonas sp.
<220> FEATURE:
<221> NAME/KEY: CDS
<222> LOCATION: (1)..(3186)

<400> SEQUENCE: 5
```

| | |
|---|---|
| atg aaa cag ttg agg acg ctg gca tgc att gcc acg ctg ggt ctc ggc<br>Met Lys Gln Leu Arg Thr Leu Ala Cys Ile Ala Thr Leu Gly Leu Gly<br>1                  5                  10                  15 | 48 |
| gtg tcc ggc atc atg agc ccg gcc gcg gcc gcc gag aac tgg cca atg<br>Val Ser Gly Ile Met Ser Pro Ala Ala Ala Ala Glu Asn Trp Pro Met<br>              20                  25                  30 | 96 |
| ttc ggc aag aac tat gag aat tca cga gcc acg gcc gac acc cag ctc<br>Phe Gly Lys Asn Tyr Glu Asn Ser Arg Ala Thr Ala Asp Thr Gln Leu<br>35                  40                  45 | 144 |
| tct aca tcc aac att tct tcg ctc aac gtc gtg cgt cgc acg gcc gac<br>Ser Thr Ser Asn Ile Ser Ser Leu Asn Val Val Arg Arg Thr Ala Asp<br>50                  55                  60 | 192 |

-continued

| | | |
|---|---|---|
| ggc ggc atc acg gga aca ccg acc gtc gtt gac ggc gtg gcg tat tac<br>Gly Gly Ile Thr Gly Thr Pro Thr Val Val Asp Gly Val Ala Tyr Tyr<br>65                             70                        75                    80 | | 240 |
| tcg gat ttt tcg ggc tat gtg aag gcc gtg cgt gtg aat gac ggc gcc<br>Ser Asp Phe Ser Gly Tyr Val Lys Ala Val Arg Val Asn Asp Gly Ala<br>                    85                        90                        95 | | 288 |
| gtg ctg tgg cgt gtg cgc ccg cag acg acg atg ctc tcg cca tcg ccc<br>Val Leu Trp Arg Val Arg Pro Gln Thr Thr Met Leu Ser Pro Ser Pro<br>              100                      105                      110 | | 336 |
| ttc gtc acc gac gac acg gtc tat gtc gcc ggc aac aac tcg tat gta<br>Phe Val Thr Asp Asp Thr Val Tyr Val Ala Gly Asn Asn Ser Tyr Val<br>              115                      120                      125 | | 384 |
| tat gca ctc aac cgc ctc gac ggc gca gtg cgc tgg acg acg cag atc<br>Tyr Ala Leu Asn Arg Leu Asp Gly Ala Val Arg Trp Thr Thr Gln Ile<br>130                            135                      140 | | 432 |
| gaa act tcg ccg aac agc cgc atc tct tcc tcg ccg atc gtg gtc gac<br>Glu Thr Ser Pro Asn Ser Arg Ile Ser Ser Ser Pro Ile Val Val Asp<br>145                            150                      155                      160 | | 480 |
| aac atc ctg atg atc ggt acg ggt tcc tat cag gtg ttc att ccc gcg<br>Asn Ile Leu Met Ile Gly Thr Gly Ser Tyr Gln Val Phe Ile Pro Ala<br>                    165                      170                      175 | | 528 |
| acg ccg atg ttc cgg gga cgc gtc gtc ttc ctg aac gcg acg acg ggc<br>Thr Pro Met Phe Arg Gly Arg Val Val Phe Leu Asn Ala Thr Thr Gly<br>              180                      185                      190 | | 576 |
| gcc atc ctg cct tac agc acc aac atg tgt ccg gaa ggc ctg tgt ggc<br>Ala Ile Leu Pro Tyr Ser Thr Asn Met Cys Pro Glu Gly Leu Cys Gly<br>                195                      200                      205 | | 624 |
| ggc ggc atc tcg gtg tgg tcg acc gcg gcc gtc gat gtg tcg acg cgc<br>Gly Gly Ile Ser Val Trp Ser Thr Ala Ala Val Asp Val Ser Thr Arg<br>210                            215                      220 | | 672 |
| acc ggc tat atc ggt acc gga cag gct tat aga gat ccc gcg ggt ccg<br>Thr Gly Tyr Ile Gly Thr Gly Gln Ala Tyr Arg Asp Pro Ala Gly Pro<br>225                            230                      235                      240 | | 720 |
| tac tcg gac tcg ctg gtt gcg ttt gat atc gac acg ggc gcg att cgc<br>Tyr Ser Asp Ser Leu Val Ala Phe Asp Ile Asp Thr Gly Ala Ile Arg<br>                    245                      250                      255 | | 768 |
| tgg tcg cag cag ttc ctg gcc aac gac gtg tat cag ctg ggc ggc gta<br>Trp Ser Gln Gln Phe Leu Ala Asn Asp Val Tyr Gln Leu Gly Gly Val<br>              260                      265                      270 | | 816 |
| ctg cgt tac gac tac gac gtc ggc gct gcg ccg aat ctg ttc gtg gca<br>Leu Arg Tyr Asp Tyr Asp Val Gly Ala Ala Pro Asn Leu Phe Val Ala<br>                275                      280                      285 | | 864 |
| gat gag cgc cgc atg gtt ggc gtt ggc ggc aag gac ggc acc tat cgg<br>Asp Glu Arg Arg Met Val Gly Val Gly Gly Lys Asp Gly Thr Tyr Arg<br>290                            295                      300 | | 912 |
| gcc ttc gat cgt gat acc ggt gcg ccg atc tgg acc act ccg gta gga<br>Ala Phe Asp Arg Asp Thr Gly Ala Pro Ile Trp Thr Thr Pro Val Gly<br>305                            310                      315                      320 | | 960 |
| cgc ggc agt ccc atc ggc gga gtg atg cag tcg acg gcg tat ggc gac<br>Arg Gly Ser Pro Ile Gly Gly Val Met Gln Ser Thr Ala Tyr Gly Asp<br>                    325                      330                      335 | | 1008 |
| ggc cgc atc tac gtg acc agc aat act tcg acg att ggc ggc ggt cgc<br>Gly Arg Ile Tyr Val Thr Ser Asn Thr Ser Thr Ile Gly Gly Gly Arg<br>                    340                      345                      350 | | 1056 |
| aat gat ccc gtg cct gca acg gcc gaa gcg ctg gcg ctc gat gcc gcg<br>Asn Asp Pro Val Pro Ala Thr Ala Glu Ala Leu Ala Leu Asp Ala Ala<br>                355                      360                      365 | | 1104 |
| acc ggc acg ccg gtg tgg ata cgt cag ctc gac gct ggc ggt ttc ggc<br>Thr Gly Thr Pro Val Trp Ile Arg Gln Leu Asp Ala Gly Gly Phe Gly<br>370                            375                      380 | | 1152 |

```
ggc gtt gcc tac gcg aac ggg ctg atg tac gcc tcg gtg tgg gat ggc      1200
Gly Val Ala Tyr Ala Asn Gly Leu Met Tyr Ala Ser Val Trp Asp Gly
385                 390                 395                 400 cgg atg cgg gtg ttc aat gcc gcc aat ggc aac atc gtc aag gaa gtg      1248
Arg Met Arg Val Phe Asn Ala Ala Asn Gly Asn Ile Val Lys Glu Val
            405                 410                 415 cag gtt tcg ccg tcg cgc ggg gtc tat gtg gcg gcg ccg acg gac gga      1296
Gln Val Ser Pro Ser Arg Gly Val Tyr Val Ala Ala Pro Thr Asp Gly
        420                 425                 430 ttc ccg aac ggc tcg gcg ggc ggc ccg atc gtg tac ggc aat cgc gtg      1344
Phe Pro Asn Gly Ser Ala Gly Gly Pro Ile Val Tyr Gly Asn Arg Val
    435                 440                 445 ctg atg ggc tac ggc tgg acg tgg gtg ctc aac atc agc ggt ggt ctg      1392
Leu Met Gly Tyr Gly Trp Thr Trp Val Leu Asn Ile Ser Gly Gly Leu
450                 455                 460 gcg acc atg gaa ctg gtc tct ggt ggc gga gag acg cag acg gtc aca      1440
Ala Thr Met Glu Leu Val Ser Gly Gly Gly Glu Thr Gln Thr Val Thr
465                 470                 475                 480 ctg gcg tcg aat cag gac acc tat gtc cag agc ggc acg ccg acg acg      1488
Leu Ala Ser Asn Gln Asp Thr Tyr Val Gln Ser Gly Thr Pro Thr Thr
            485                 490                 495 agc tac aac gcc aac gag ttt ctg ctg gcg cga ctc gcg gat gcg gaa      1536
Ser Tyr Asn Ala Asn Glu Phe Leu Leu Ala Arg Leu Ala Asp Ala Glu
        500                 505                 510 ggg ctg acg cgg gcg tca ttc ctg cag ttt ccg ctg aca gcg att ccg      1584
Gly Leu Thr Arg Ala Ser Phe Leu Gln Phe Pro Leu Thr Ala Ile Pro
    515                 520                 525 gct ggc acg atc acg tcg gcc cgc ctg cgg ctc tat ggc cgt cat gat      1632
Ala Gly Thr Ile Thr Ser Ala Arg Leu Arg Leu Tyr Gly Arg His Asp
530                 535                 540 gcg ccg acc gga acg ggt cag cct gtg tcg gta tgg ccg ggc acc ttc      1680
Ala Pro Thr Gly Thr Gly Gln Pro Val Ser Val Trp Pro Gly Thr Phe
545                 550                 555                 560 acg acg ccg tgg aat ggc gca gac gtc atc tac aac aac tcc gac ctg      1728
Thr Thr Pro Trp Asn Gly Ala Asp Val Ile Tyr Asn Asn Ser Asp Leu
            565                 570                 575 gta acg ggc gtc aat ttc tat ctg acc agc ccc att gcg aat gcg ctc      1776
Val Thr Gly Val Asn Phe Tyr Leu Thr Ser Pro Ile Ala Asn Ala Leu
        580                 585                 590 atc ggc atc acg ccg cag tac tac gag tgg gac gtg acg ggc tat gtg      1824
Ile Gly Ile Thr Pro Gln Tyr Tyr Glu Trp Asp Val Thr Gly Tyr Val
    595                 600                 605 gat tcg cgc cgg gcg ctg ggt cat gcg acg ttc ggt gtc gcg gtc gac      1872
Asp Ser Arg Arg Ala Leu Gly His Ala Thr Phe Gly Val Ala Val Asp
610                 615                 620 tac ggc cat ctg tac cgg gtg acg ttc aat tcc gcg gac aat gcc gcg      1920
Tyr Gly His Leu Tyr Arg Val Thr Phe Asn Ser Ala Asp Asn Ala Ala
625                 630                 635                 640 aat cgg ccg gag ctc gtc gtg gcg gtg agc acc ggt ggc acc agt gag      1968
Asn Arg Pro Glu Leu Val Val Ala Val Ser Thr Gly Gly Thr Ser Glu
            645                 650                 655 ccc gat ccc gag ttg ccg ccc gga agc atg gaa ggc agc tgt ccc gcg      2016
Pro Asp Pro Glu Leu Pro Pro Gly Ser Met Glu Gly Ser Cys Pro Ala
        660                 665                 670 ggg ttc acg ccg cgg gcc ggc gtc aat cag ggc ttc ata cac aac ggc      2064
Gly Phe Thr Pro Arg Ala Gly Val Asn Gln Gly Phe Ile His Asn Gly
    675                 680                 685 gtg gcg cgc gga ttc gtg ctg aac gtg ccg gcg aat gtc tct act ccg      2112
Val Ala Arg Gly Phe Val Leu Asn Val Pro Ala Asn Val Ser Thr Pro
```

-continued

|  |  |  |
|---|---|---|
| 690 | 695 | 700 |

| cgt ccg atg ttc gtc tcg ctc acc ggt tcg gtc gaa tcg acg aac gag | 2160 |
| Arg Pro Met Phe Val Ser Leu Thr Gly Ser Val Glu Ser Thr Asn Glu | |
| 705 710 715 720 | |

| aac ctg gga cca cgt ggc ggc gcc ggt gcg ctc acc aat gac ggc ttc | 2208 |
| Asn Leu Gly Pro Arg Gly Gly Ala Gly Ala Leu Thr Asn Asp Gly Phe | |
| 725 730 735 | |

| ctg gtc atc ggc ccc gtg cgt cgc tgt gcg ggc cag gat ccg aac ggt | 2256 |
| Leu Val Ile Gly Pro Val Arg Arg Cys Ala Gly Gln Asp Pro Asn Gly | |
| 740 745 750 | |

| agc ggg acc agc gtc ggc ggc gga acc tgc aat cag cca ggt acg ggc | 2304 |
| Ser Gly Thr Ser Val Gly Gly Gly Thr Cys Asn Gln Pro Gly Thr Gly | |
| 755 760 765 | |

| gga tgg aac tgg aat ccg tgg aat gag ggt cgc gcg ttc ggc gct gcc | 2352 |
| Gly Trp Asn Trp Asn Pro Trp Asn Glu Gly Arg Ala Phe Gly Ala Ala | |
| 770 775 780 | |

| ggc gat cag tgg aag act gct gaa ggt ccg gac tcc gag ttc ctc gag | 2400 |
| Gly Asp Gln Trp Lys Thr Ala Glu Gly Pro Asp Ser Glu Phe Leu Glu | |
| 785 790 795 800 | |

| tcg gtc gcg cgc tgc gtg gcg aag cgc ttc ccg gtc gat tcg aag cgc | 2448 |
| Ser Val Ala Arg Cys Val Ala Lys Arg Phe Pro Val Asp Ser Lys Arg | |
| 805 810 815 | |

| atg tac ctc ggc ggc att tcc ggc ggc aca ctg acc aat cgt gcg | 2496 |
| Met Tyr Leu Gly Gly Ile Ser Ser Gly Gly Thr Leu Thr Asn Arg Ala | |
| 820 825 830 | |

| ttg ctg ttc aac tcg gac ttc tgg gcg ggc ggc ctg ccg atc tcg ggt | 2544 |
| Leu Leu Phe Asn Ser Asp Phe Trp Ala Gly Gly Leu Pro Ile Ser Gly | |
| 835 840 845 | |

| gag tgg tac gtc acc cgc gac gac ggc acc gcc tat ccg ggt ccg gat | 2592 |
| Glu Trp Tyr Val Thr Arg Asp Asp Gly Thr Ala Tyr Pro Gly Pro Asp | |
| 850 855 860 | |

| gaa ttc gcc gcg cgg cgc cag gcc gtg atc gac gat ccg acc aag atc | 2640 |
| Glu Phe Ala Ala Arg Arg Gln Ala Val Ile Asp Asp Pro Thr Lys Ile | |
| 865 870 875 880 | |

| ttc cag gga cgg gtc ggt ccg ctg ccg ctg cgc tca acg ctg gat ccg | 2688 |
| Phe Gln Gly Arg Val Gly Pro Leu Pro Leu Arg Ser Thr Leu Asp Pro | |
| 885 890 895 | |

| atg atc gtg atc acg gtc tgg ggt ggc acg aac gat gtg tgg agc tgc | 2736 |
| Met Ile Val Ile Thr Val Trp Gly Gly Thr Asn Asp Val Trp Ser Cys | |
| 900 905 910 | |

| gac ggc gtc acc ctg tgt gcc gac tac aga cca agc acg cag gta gcg | 2784 |
| Asp Gly Val Thr Leu Cys Ala Asp Tyr Arg Pro Ser Thr Gln Val Ala | |
| 915 920 925 | |

| tcc aac tac ttc agt gcg cag ccc aat gtc gtc cac gtg gcc tgc tcg | 2832 |
| Ser Asn Tyr Phe Ser Ala Gln Pro Asn Val Val His Val Ala Cys Ser | |
| 930 935 940 | |

| tcg agt cac ggt cat caa tgg ccg acc ata aac cgc gct gca ttc aat | 2880 |
| Ser Ser His Gly His Gln Trp Pro Thr Ile Asn Arg Ala Ala Phe Asn | |
| 945 950 955 960 | |

| acg tgg gct gcc acg acg ctg gcc tcg cat ccg aag gga acg ccg gct | 2928 |
| Thr Trp Ala Ala Thr Thr Leu Ala Ser His Pro Lys Gly Thr Pro Ala | |
| 965 970 975 | |

| tct gca ttc gtg ctg ccg ccg ccg gcg ggt tac acc tgc cgc atc | 2976 |
| Ser Ala Phe Val Leu Pro Pro Pro Ala Gly Tyr Thr Cys Arg Ile | |
| 980 985 990 | |

| ggt ccc tac atc gat cac tac gag cgc gcc tgc tcg gtc gat ggg gac | 3024 |
| Gly Pro Tyr Ile Asp His Tyr Glu Arg Ala Cys Ser Val Asp Gly Asp | |
| 995 1000 1005 | |

| ggt gat atc gac cgg aat gac atc gcg gtg atc act gcc gcc cgc | 3069 |

|  |  |  |  |  |  |  |  |  |  |  |
|---|---|---|---|---|---|---|---|---|---|---|
| Gly | Asp | Ile | Asp | Arg | Asn | Asp | Ile | Ala | Val | Ile | Thr | Ala | Ala | Arg |
| 1010 | | | | | 1015 | | | | | 1020 |

```
aac cag ccg gcg tca ggc ccc acg gat ctg cgc gac gta gat cgc      3114
Asn Gln Pro Ala Ser Gly Pro Thr Asp Leu Arg Asp Val Asp Arg
    1025                1030                1035 agt ggc gtg atc gat gtc aac gat gcg cgt gcc tgc acg ctg cgc      3159
Ser Gly Val Ile Asp Val Asn Asp Ala Arg Ala Cys Thr Leu Arg
1040                1045                1050 tgt gac cgt ccc aat tgc gca gtc cag                              3186
Cys Asp Arg Pro Asn Cys Ala Val Gln
        1055                1060

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
catatgtata tctccttctt aaag                                         24

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
catggtatgg ctagcatgac tgg                                          23

<210> SEQ ID NO 8
<211> LENGTH: 42
<212> TYPE: DNA
<213> ORGANISM: Artificial Sequence
<220> FEATURE:
<223> OTHER INFORMATION: Synthetic

<400> SEQUENCE: 8
taagaaggag atatacatat ggccgagaac tggccaatgt tc                     42

<210> SEQ ID NO 9
<211> LENGTH: 39
<212> TYPE: DNA
<213> ORGANISM: Artificial Sequence
<220> FEATURE:
<223> OTHER INFORMATION: Synthetic

<400> SEQUENCE: 9
atgctagcca tacccatgtt actggactgc gcaattggg                         39

<210> SEQ ID NO 10
<211> LENGTH: 41
<212> TYPE: DNA
<213> ORGANISM: Artificial Sequence
<220> FEATURE:
<223> OTHER INFORMATION: Synthetic

<400> SEQUENCE: 10
catgctagcc ataccatgtc acgttccgct gtagtgatcc g                      41

<210> SEQ ID NO 11
<211> LENGTH: 20
<212> TYPE: PRT
```

```
<213> ORGANISM: Pseudomonas sp.

<400> SEQUENCE: 11

Ala Glu Asn Trp Pro Met Phe Gly Lys Asn Tyr Glu Asn Thr Arg Ala
1               5                   10                  15

Thr Ser Asp Thr
            20

<210> SEQ ID NO 12
<211> LENGTH: 20
<212> TYPE: PRT
<213> ORGANISM: Pseudomonas sp.

<400> SEQUENCE: 12

Ala Glu Asn Trp Pro Met Phe Gly Lys Asn Tyr Glu Asn Ser Arg Ala
1               5                   10                  15

Thr Ala Asp Thr
            20

<210> SEQ ID NO 13
<211> LENGTH: 526
<212> TYPE: PRT
<213> ORGANISM: Pseudomonas sp.

<400> SEQUENCE: 13

Pro His Ala Ile Trp Gly Pro Ser Ala Ser Met Pro Leu Asp Gly
1               5                   10                  15

Pro Lys Cys Lys Gly Lys Ile Pro Pro Ile Asp Leu Ser Thr Pro Asp
            20                  25                  30

Gln Trp Asn Gly Trp Gly Ala Gly Ile Thr Asn Ala Arg Phe Gln Pro
        35                  40                  45

Asn Pro Gly Leu Thr Ala Ala Asp Val Pro Arg Leu Lys Val Lys Trp
    50                  55                  60

Ala Phe Asn Tyr Pro Gly Ser Lys Asn Gly Gln Ala Thr Val Val Gly
65                  70                  75                  80

Asp Arg Leu Phe Val Thr Ser Met Ser Gly Ala Val Tyr Ala Leu Asn
                85                  90                  95

Ala Lys Thr Gly Cys Val Tyr Trp Arg His Asp Ala Ala Ala Ala Thr
            100                 105                 110

Arg Ser Ser Val His Val Gln Leu Pro Ala Gly Ala Pro Ala Gln
        115                 120                 125

Tyr Ala Ile Phe Phe Ser Asp Trp Thr Lys Ala Val Ala Leu Asp
    130                 135                 140

Ala Gln Thr Gly Lys Gln Leu Trp Lys Thr Thr Ile Asp Asp Gln Pro
145                 150                 155                 160

Gly Val Gln Met Thr Gly Ser Pro Thr Tyr His Glu Gly Lys Leu Phe
                165                 170                 175

Val Pro Ile Ser Ser Gly Asn Glu Ala Phe Ala Thr Asn Asp Gln Trp
            180                 185                 190

Glu Cys Cys Lys Phe Arg Gly Ala Leu Val Ala Leu Asp Ala Leu Ser
        195                 200                 205

Gly Lys Val Leu Trp Lys Thr Tyr Thr Thr Gln Lys Glu Pro Ala Pro
    210                 215                 220

Phe Arg Leu Asn Lys Leu Gly Lys Gln Met Trp Gly Pro Ala Gly
225                 230                 235                 240

Ser Ile Trp Ser Ala Pro Thr Ile Asp Pro Lys Arg Gly Leu Val Tyr
                245                 250                 255
```

-continued

Val Ala Thr Ser Asn Ser Tyr Thr Glu Val His His Glu Gly Ser Asp
            260                 265                 270

Ala Val Met Ala Met Glu Ile Glu Thr Gly Lys Val Arg Trp Ile Asn
            275                 280                 285

Gln Val Thr Lys Asp Asp Asn Tyr Ile Ile Gly Cys Pro Arg Ala Ala
    290                 295                 300

Asn Cys Pro Glu Lys Val Gly Pro Asp Phe Ala Leu Gly Asn Ser Pro
305                 310                 315                 320

Ile Leu His Thr Leu Gln Asp Gly Arg Gln Tyr Ile Val Val Gly Gln
                325                 330                 335

Lys Ser Gly Ala Val Tyr Ala Met Asp Pro Asp Asn Asp Gly Glu Leu
            340                 345                 350

Ile Trp Met Arg Arg Val Ser Pro Gly Ser Glu Leu Gly Gly Val Glu
            355                 360                 365

Phe Gly Met Ala Ala Asp Ala Glu Asn Val Tyr Val Gly Ile Ser Asp
    370                 375                 380

Val Ile Thr Arg Lys Gly Gly Lys Pro Gly Val Tyr Ala Leu Arg Ile
385                 390                 395                 400

Arg Asp Gly Ala Asp Val Trp Ala Phe Pro Ala Pro Arg Thr Pro Cys
                405                 410                 415

Arg Trp Asn Asn Ile Phe Cys His Pro Ala Val Ser Gln Ala Val Thr
            420                 425                 430

Ala Met Pro Gly Val Val Phe Ala Gly Ser Met Asp Gly His Phe Arg
    435                 440                 445

Ala Phe Ser Thr Ser Asp Gly Lys Val Leu Trp Glu Phe Asn Thr Ala
450                 455                 460

Ala Ala Pro Tyr Lys Thr Val Ala Gly Lys Gln Ala Asp Gly Gly Val
                465                 470                 475                 480

Met Asp Gly Ala Gly Pro Thr Ile Ala Gly Gly Met Val Tyr Val His
            485                 490                 495

Ser Gly Tyr Ala Gly Arg Ser Thr Gln Asn Ala Gly Asp Leu Arg Gly
    500                 505                 510

Arg Glu Gly Asn Val Leu Ile Ala Phe Ser Val Asp Gly Lys
            515                 520                 525

<210> SEQ ID NO 14
<211> LENGTH: 534
<212> TYPE: PRT
<213> ORGANISM: Pseudomonas sp.

<400> SEQUENCE: 14

Leu Arg Arg Ile Trp Gly Asn Ser Val Glu Gly Thr Pro Leu Asp Ala
1               5                   10                  15

Pro Gln Cys Ser Ser Ala Pro Thr Pro Val Asp Leu Gly Ala Ala Asn
                20                  25                  30

Gln Trp Asn Gly Trp Ser Thr Glu Lys Asp Asn Gly Arg Phe Gln Arg
            35                  40                  45

Lys Pro Ala Leu Asp Val Ala Asp Ile Pro Lys Leu Lys Leu Lys Trp
    50                  55                  60

Ala Phe Gln Tyr Pro Gly Ser Lys Asn Gly Gln Ala Thr Val Ile Gly
65                  70                  75                  80

Asp Arg Leu Phe Thr Thr Ser Thr Ser Gly Ala Val Tyr Ala Leu Asn
                85                  90                  95

Ala Lys Thr Gly Cys Val Tyr Trp Arg His Ala Ala Glu Gly Ala Thr

```
                100                 105                 110
Arg Thr Ser Pro Val Ile Ala Ala Leu Pro Glu Gly Ala Pro Ala Lys
            115                 120                 125

Thr Ala Leu Phe Phe Ser Asp Phe Thr Lys Ala Ala Val Ala Leu Asp
            130                 135                 140

Ala Glu Thr Gly Lys Gln Leu Trp Lys Thr Val Val Asp Asp Gln Pro
145                 150                 155                 160

Ala Leu Gln Met Thr Gly Ser Ile Thr Tyr Trp Asp Gly Lys Ile Tyr
                165                 170                 175

Val Pro Ile Ser Ser Gly Thr Glu Ala Phe Ala Gln Ile Pro Thr Trp
                180                 185                 190

Glu Cys Cys Lys Phe Arg Gly Ala Leu Val Ala Leu Asp Ala Ala Thr
                195                 200                 205

Gly Lys Ile Leu Trp Lys Arg Tyr Thr Thr Gln Glu Pro Arg Pro
210                 215                 220

Phe Lys Leu Asn Lys Ala Gly Arg Gln Met Trp Gly Pro Ser Gly Gly
225                 230                 235                 240

Ala Ile Trp Val Thr Pro Thr Val Asp Glu Ala Arg Arg Leu Ile Tyr
                245                 250                 255

Val Gly Thr Ser Asn Ser Tyr Thr Asp Val Pro Tyr Asp Asn Ser Asp
                260                 265                 270

Ser Val Met Ala Ile Asp Ala Asp Thr Gly Ala Val Arg Trp Thr Val
                275                 280                 285

Gln Leu Leu Ala Asp Asp Asn Tyr Ile Asp Gly Cys Trp Gln Lys Gly
                290                 295                 300

Lys Glu His Ala Asn Cys Pro Asn Pro Leu Gly Pro Asp Phe Ser Ile
305                 310                 315                 320

Gly Ala Ala Pro Ile Tyr Arg Lys Met Ala Asp Gly Lys Glu Phe Leu
                325                 330                 335

Leu Val Gly Gln Lys Ser Gly Met Ile Tyr Ala Leu Asp Pro Ala Asn
                340                 345                 350

Lys Gly Ala Lys Ile Trp Glu Arg Gln Leu Ser Leu Gly Ser Ala Leu
                355                 360                 365

Gly Gly Ile Glu Phe Gly Thr Ala Ala Asp Asp Gly Lys Val Tyr Ala
                370                 375                 380

Gly Val Ser Asp Ile Ala Ser Gln Ala Lys Asp Arg Gly Lys Pro Gly
385                 390                 395                 400

Leu Trp Ala Leu Asp Ile Arg Thr Gly Glu Val Ala Trp Asn Phe Leu
                405                 410                 415

Asn Ala Pro Asp Thr Lys Cys Arg Trp Asn Asn Trp Trp Cys His Gly
                420                 425                 430

Ala Phe Ser Gln Ala Ile Ser Val Ile Pro Gly Ala Ile Phe Ala Gly
                435                 440                 445

Ser Tyr Asp Gly His Phe Arg Ala Phe Asp Thr Ala Thr Gly Lys Ile
                450                 455                 460

Ile Trp Asp Val Asp Thr Gly Thr Lys Ala Val Thr Thr Leu Ser Gly
465                 470                 475                 480

Ala Lys Ala Phe Gly Gly Val Met Asp Gly Ala Gly Pro Thr Ile Ala
                485                 490                 495

Gly Gly Met Val Tyr Val His Ser Gly Tyr Ala Gly Arg Ser Ser Glu
                500                 505                 510

Ser Gly Gly Arg Asp Leu Arg Gly Thr Asp Gly Asn Ile Leu Met Ala
                515                 520                 525
```

```
Phe Ser Val Asp Gly Lys
    530

<210> SEQ ID NO 15
<211> LENGTH: 379
<212> TYPE: PRT
<213> ORGANISM: Pseudomonas sp.

<400> SEQUENCE: 15

Met Asn Gln Ser Leu Gly Val Leu Arg Leu Thr Arg Gly Val Ile Ala
1               5                   10                  15

Leu Ala Leu Ala Ser Val Ala Ser Gly Cys Ser Ser Thr Gly Ala Asp
            20                  25                  30

Arg Thr Ala Ala Thr Pro Ala Ala Asn Pro Ala Ala Thr Glu Pro
        35                  40                  45

Val Lys Trp Glu Cys Pro Ala Gly Tyr Glu Val Lys Glu Gly Leu Asn
    50                  55                  60

Val Asp Phe Pro His Lys Gly Met Lys Arg Ala Phe Ile Val Tyr Pro
65                  70                  75                  80

Ala Lys Asn Val Ser Gly Pro Ala Pro Val Trp Val Pro Met Thr Gly
                85                  90                  95

Ser Val Glu Ser Thr Asn Asp Asn Leu Thr Val Ala Arg Ser Gly Ala
            100                 105                 110

Asn Ser Ile Leu Ala Asp His Gly Tyr Thr Val Ile Ala Pro Val Arg
        115                 120                 125

Ala Cys Ala Asn Gln Asp Pro Asn Ile Arg Gly Glu Arg Cys Asn Gly
130                 135                 140

Pro Gly Ser Asn Gly Trp Asn Trp Asn Pro Trp Phe Glu Gly Arg Ala
145                 150                 155                 160

Ala Asp Pro Ser Gly Glu His Trp Lys Asn Asp Glu Gly Pro Asp Ser
                165                 170                 175

Ser Phe Phe Val Ala Met Val Gln Cys Val Gly Thr Lys Tyr Lys Leu
            180                 185                 190

Asp Ala Arg Arg Leu Phe Leu Gly Gly Ile Ser Ser Gly Gly Thr Met
        195                 200                 205

Thr Asn Arg Ala Leu Leu Phe Arg Ser Asn Phe Trp Ala Gly Gly Leu
210                 215                 220

Pro Ile Ser Gly Glu Trp Tyr Val Thr Ser Asp Asp Gly Thr Pro Leu
225                 230                 235                 240

Ser Phe Asp Asp Ala Arg Ala Ala Val Ala Ala Pro Thr Lys Ile
                245                 250                 255

His Gln Gly Arg Val Gly Pro Tyr Pro Leu Pro Ala Lys Val Gly Pro
            260                 265                 270

Leu Ile Val Met Thr Val Trp Gly Gly Glu Lys Asp Leu Trp Asn Cys
        275                 280                 285

Thr Arg Pro Asp Gly Ser Arg Phe Leu Cys Ala Asp Tyr Arg Pro Ser
290                 295                 300

Thr Gln Ala Gly Ser Asn Phe Phe Ser Ala Gln Pro Asp Val Val His
305                 310                 315                 320

Val Ala Cys Ser Ser Thr His Gly His Met Trp Pro Gln Leu Asn Thr
                325                 330                 335

Gln Glu Phe Asn Arg Trp Ala Leu Asp Thr Leu Ala Ser His Pro Lys
            340                 345                 350

Gly Ser Asp Pro Arg Ser Phe Lys Leu Thr Gln Pro Pro Glu Gly Tyr
```

```
                355                 360                 365
Thr Cys His Val Gly Pro Phe Thr Gly Leu Tyr
            370                 375

<210> SEQ ID NO 16
<211> LENGTH: 364
<212> TYPE: PRT
<213> ORGANISM: Pseudomonas sp.

<400> SEQUENCE: 16

Met Phe Lys Pro Val Lys Ser Arg Ser Arg Ser Phe Cys Tyr
1               5                   10                  15

Leu Ala Gly Cys Leu Ala Met Val Ala Thr Leu Ser Ser Thr Ala
                20                  25                  30

Gln Ala Lys Ser Glu Trp Ala Cys Pro Glu Gly Phe Thr Pro Lys Ala
            35                  40                  45

Gly Leu Asn Thr Asp Phe Pro Ser Asp Gly Lys Lys Arg Ala Phe Val
        50                  55                  60

Val Val Pro Pro Lys Asp Ser Ala Gly Gly Ala Pro Val Trp Val Pro
65                  70                  75                  80

Met Val Gly Thr Val Glu Ala Thr Asn Trp Asn Leu Asn Val Pro Arg
                85                  90                  95

Ser Gly Asn Asn Ala Lys Leu Ala Glu His Gly Tyr Met Val Ile Ser
            100                 105                 110

Pro Val Arg Gln Cys Ala Glu Gln Asp Pro Asn Leu Gly Ala Gly Ala
        115                 120                 125

Cys Asn Gly Val Gly Lys Asp Gly Trp Thr Trp Asn Pro Trp Asn Asp
130                 135                 140

Gly Arg Ala Pro Asp Ala Ser Gly Asp Lys Tyr Lys Thr Asp Ala Gly
145                 150                 155                 160

Asp Asp Val Arg Phe Leu Glu Ala Met Val Arg Cys Val Gly Thr Lys
                165                 170                 175

Trp Lys Leu Asp Arg Lys Arg Leu Phe Leu Gly Gly Ile Ser Ala Gly
            180                 185                 190

Gly Thr Met Thr Asn Arg Ala Leu Leu Phe Asp Ser Glu Phe Trp Ala
        195                 200                 205

Gly Gly Met Pro Ile Ser Gly Glu Trp Tyr Ser Thr Lys Asp Asp Gly
210                 215                 220

Ser Thr Val Pro Phe Gln Glu Thr Arg Lys Met Val Ala Ala Ala Pro
225                 230                 235                 240

Ala Lys Ile Trp Gln Gly Arg Val Gly Pro Tyr Pro Leu Pro Ser Lys
                245                 250                 255

Leu Asp Pro Met Val Val Ile Thr Val Trp Gly Gly Glu Lys Asp Leu
            260                 265                 270

Trp Asp Cys Gly Pro Pro Leu Gly Leu Cys Ser Asp Tyr Arg Pro Thr
        275                 280                 285

Thr Gln Ala Ser Ser Asn Tyr Phe Ser Ser Ile Ser Asn Val Val His
        290                 295                 300

Val Ala Cys Ser Ala Thr His Gly His Met Trp Pro Gln Val Asn Thr
305                 310                 315                 320

Asp Ala Phe Asn Leu Trp Ala Leu Asn Thr Met Ala Ser His Pro Lys
                325                 330                 335

Gly Ser Ser Pro Lys Asp Phe Lys Leu Thr Ala Pro Pro Glu Gly Tyr
            340                 345                 350
```

```
Ser Cys Lys Ile Gly Arg Phe Thr Asp His Tyr Lys
    355                 360
```

POLYVINYL ALCOHOL-DEGRADING ENZYME AND PROCESS FOR PRODUCING THE SAME

The Sequence Listing in ASCII text file format of 64,714 bytes in size, created on May 4, 2023, with the file name "2023-05-04SequenceListing_YAMANAKA14A," filed in the U.S. Patent and Trademark Office on even date herewith, is hereby incorporated herein by reference.

TECHNICAL FIELD

The present invention relates to a polyvinyl alcohol-degrading enzyme and a process for producing the same, particularly, to a novel polyvinyl alcohol-degrading enzyme and a process for producing the same; and a DNA encoding the enzyme, a recombinant DNA comprising the DNA, and a transformant having the recombinant DNA.

BACKGROUND ART

Polyvinyl alcohol (hereinafter, abbreviated as "PVA" in this specification) is a water-soluble polymer which can be obtained by saponification (alkali hydrolysis) of polyvinyl acetate, a polymer obtained by polymerizing a monomer of vinyl acetate. Since PVA has excellent properties such as adhesion, stickiness, film-forming, coating, surface activity; and has a high chemical stability, it has been industrially widely used as a material of vinylon fibers, fiber sizing agents, paper processing agents, adhesives, films, polymerization auxiliary, etc. However, in applications such as fiber sizing agents, it is necessary to remove PVA from fibers after use. Since a large amount of water and chemicals are required for removing PVA, the increase of the cost and the environment load are inevitable. In addition, PVA has the disadvantage that it is difficult to decompose in the nature because it is a synthetic polymer.

As a means to decompose PVA, a number of attempts of isolating microorganisms having a PVA-degrading activity from the activated sludge for processing the factory waste containing PVA, and decomposing PVA using the microorganism, have been reported. As microorganisms having a PVA-degrading activity, Patent literatures 1 to 5 have disclosed bacteria such as *Pseudomonas, Acinetobacter, Sphingopyxis* (formerly classified into *Sphingomonas* or *Pseudomonas*), Comamonas (purple bacteria, photosynthetic bacteria), *Microbacterium, Enterobacter, Corynebacterium, Rhodococcus, Caseobactor, Xanthomonas, Neisseria, Bacillus, Brevibacterium, Escherichia, Aerobacter, Alcaligenes, Agrobacterium, Arthrobacter, Paenibacillus, Cardiobacterium, Streptomyces, Polaribacter* (formerly classified as *Steroidobacter*), *Thalassospira* etc.; fungi such as *Penicillium, Geotrichum*, etc., and Basidiomycetes.

It has been reported that the degradation of PVA by microorganisms is generally performed by the joint action of a PVA-oxidizing enzyme and an oxidized PVA-hydrolyzing enzyme (See Non-Patent Literature 1). The enzymatic degradation mechanism of PVA is shown schematically in FIG. 1. As shown in FIG. 1, two kinds of enzymes, PVA oxidase (also called "Secondary Alcohol Oxidase") and PVA dehydrogenase (PVADH) using Pyrroloquinoline quinone (PQQ) as a coenzyme have been known as PVA-oxidizing enzymes. While, oxidized PVA-hydrolase (OPH, also called as "β-diketone hydrolase") has been known as oxidized PVA-hydrolyzing enzyme.

From the late 1970s to the early 1980s, purification and properties of the secondary alcohol oxidase (PVA oxidase) and oxidized PVA hydrolase, derived from a microorganism of the genus *Pseudomonas*, have been reported, respectively (See Non-Patent Literatures 2 and 3). The PVA oxidase has been characterized to be a single polypeptide having a molecular weight of about 50,000, and the oxidized PVA hydrolase has been characterized to be a single polypeptide having a molecular weight of about 38,000. Further, a method for efficiently separating and purifying PVA oxidase and oxidized PVA hydrolase using a specific chromatography carrier has also been reported (See Non-Patent Literature 4). Further, Patent Literature 6 disclosed "an enzyme composition" prepared from the culture of a microorganism of the genus *Pseudomonas*, and in the literature, it was described that the "enzyme composition", containing both PVA-oxidizable enzyme and oxidized PVA-hydrolyzable enzyme, can be used to remove PVA when repairing the cultural property containing PVA. For PVA dehydrogenases using PQQ as a coenzyme, the amino acid sequences have been revealed for those derived from a plurality of microorganisms (See Patent Literature 7 and Non-Patent Literature 5). For oxidized PVA hydrolase, the amino acid sequence (see Patent Literature 3) and the three-dimensional structure (See Non-Patent Literature 6) of the enzyme, derived from a microorganism of the genus *Pseudomonas*, have already been revealed. On the other hand, there have been few reports on the purification of PVA oxidase to a single level as a polypeptide and on the physicochemical properties of the enzyme. Also, the specific amino acid sequence of PVA oxidase has not been reported at all. For this reason, there are many unknown points in the entity of the conventionally known enzymes or group of enzymes involved in the decomposition of PVA. PVA-degrading enzyme whose entity is elucidated at a level sufficient to perform PVA degradation stably and efficiently in an industrial scale has not been known yet.

PRIOR ART LITERATURE

Patent Literature

Patent Literature 1: Japanese Patent Kokai No. 2004-000259
Patent Literature 2: Japanese Patent Kokai No. 2005-278639
Patent Literature 3: Japanese Patent Kokai No. 2006-042611
Patent Literature 4: Japanese Patent Kokai No. 2006-042612
Patent Literature 5: Japanese Patent Kokai No. 2006-180706
Patent Literature 6: Japanese Patent No. 5891478
Patent Literature 7: Japanese Patent Kokai No. H09-206079

Non-Patent Literature

Non-Patent Literature 1: Matsumura et al., Macromolecules, Vol. 32, pp. 7753-7761 (1999)
Non-Patent Literature 2: Morita et al., Agric. Biol. Chem., Vol. 43, pp. 1225-1235 (1979)
Non-Patent Literature 3: Sakai et al., Agric. Biol. Chem., Vol. 45, pp. 63-71 (1981)
Non-Patent Literature 4: Sakai et al., Agric. Biol. Chem., Vol. 47, pp. 153-155 (1983)
Non-Patent Literature 5: Shimao et al., Biosci. Biotechnol. Biochem., Vol. 60, pp. 1056-1062 (1996)
Non-Patent Literature 6: Yang et al., Chembiochem., Vol. 15, pp. 1882-1886 (2014)

DISCLOSURE OF INVENTION

Object of the Invention

The objects of the present invention are to provide a novel PVA-degrading enzyme whose entity is revealed at the level of the amino acid sequence, a process for producing the same, a DNA encoding the enzyme, a recombinant DNA comprising the DNA, and a transformant having the recombinant DNA; and to contribute to the stable and highly efficient degradation of PVA in an industrial scale.

Means to Attain the Object

In order to solve the above objects, the present inventors have been studied for microorganisms producing enzymes involved in degradation of PVA with the motivation for obtaining novel PVA-degrading enzymes. In the course of the studies, unexpectedly, they found that *Pseudomonas* sp. VT1B strain (NBRC110478), which has been conventionally known to produce PVA oxidase and oxidized PVA hydrolase, produces a completely novel PVA-degrading enzyme, which has both PVA-oxidizing activity and oxidized PVA-hydrolyzing activity and is able to degrade PVA solely as a hybrid enzyme. Then, they accomplished the present invention by clarifying the amino acid sequences and properties of the PVA-degrading enzymes, establishing a process for producing the enzymes, a DNA encoding the enzyme, a recombinant DNA comprising the DNA and transformants having the recombinant DNA.

The present invention solves the above objects by providing a novel PVA-degrading enzyme having the characteristics of the following (1) to (3), a process for producing the same, a DNA encoding the enzyme, a recombinant DNA comprising the DNA, and a transformant having the recombinant DNA:
  (1) having an activity of oxidizing PVA and forming hydrogen peroxide;
  (2) having an activity of hydrolyzing β-diketone; and
  (3) exhibiting a molecular weight of 100,000±20,000 in SDS-polyacrylamide gel electrophoresis.

Effect of the Invention

According to the present invention, a novel PVA-degrading enzyme of which entity was revealed to the levels of amino acid sequence and DNA, and a process for producing the same can be provided. Therefore, a merit enabling to produce the enzyme and to degrade PVA in an industrial scale more efficiently and stably can be obtained. Since the PVA-degrading enzyme is a hybrid enzyme having both PVA-oxidizing activity and oxidized PVA-hydrolyzing activity, it is not necessary to be used in combination with other enzymes. Since the enzyme is solely able to oxidize and degrade PVA, it has the advantage of being easy to use. Therefore, a novel PVA-degrading enzyme provided by the present invention can be advantageously used in wide fields being involved by PVA such as degradation of PVA, modification and improvement of PVA-containing products.

BRIEF DESCRIPTION OF DRAWINGS

FIG. 7 is a diagram showing the results of examining the homology between the amino acid sequence of the N-terminal first half of PVA-degrading enzyme of the present invention (residues 1-531 of SEQ ID NO:2 for PVA-A and residues 1-531 of SEQ ID NO:3 for PVA-B) and that of a conventionally known PVA-dehydrogenase (SEQ ID NO:13 for PVADH_VM15C and SEQ ID NO:14 for PVADH_113P3).

FIG. 8 is a diagram showing the results of examining the homology between the amino acid sequence of the C-terminal late half of PVA-degrading enzyme of the present invention (residues 541-966 of SEQ ID NO:2 for PVA-A and residues 541-1014 for PVA-B) and that of a conventionally known oxidized PVA-hydrolase (SEQ ID NO:15 for OPH_VM15C and SEQ ID NO:16 for OPH_113P3).

MODE FOR CARRYING OUT THE INVENTION

Figure 1:
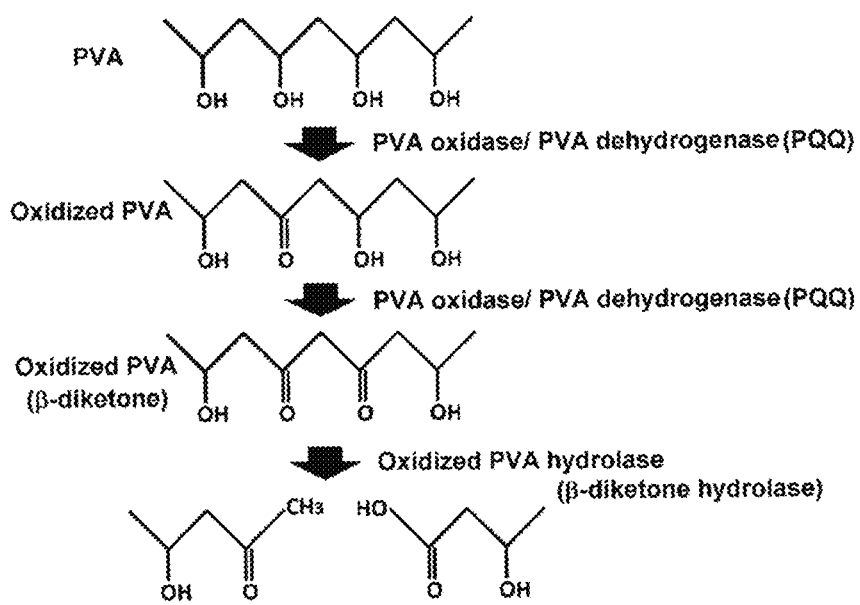
FIG. 1 is a diagram schematically showing the degradation mechanism of PVA by joint action of PVA oxidase and oxidized PVA hydrolase.

The present invention relates to a novel PVA-degrading enzyme having the characteristics of the following (1) to (3):
  (1) having an activity of oxidizing PVA and forming hydrogen peroxide;
  (2) having an activity of hydrolyzing β-diketone; and
  (3) exhibiting a molecular weight of 100,000±20,000 in SDS-polyacrylamide gel electrophoresis.

As shown in the above (1), the PVA-degrading enzyme of the present invention has an PVA-oxidizing activity, i.e., an activity of catalyzing the reaction of oxidizing PVA as substrate and forming hydrogen peroxide. For example, the PVA-oxidizing activity can be measured by the following method.

<Assay Method for PVA-Oxidizing Activity>

To 0.5 mL of a substrate solution prepared by dissolving PVA (Reagent grade polyvinyl alcohol, polymerization degree: 2,000, Nacalai Tesque Inc., Kyoto, Japan) into 100 mM sodium phosphate buffer (pH 7.0) to give a concentration of 2% (w/v), 15 □L of 2% (w/v) of sodium azide solution was added, and then 0.5 mL of an enzyme solution is further added and reacted with shaking at 27° C. for 60 min. After the 60 min-reaction, the reaction was stopped by mixing 0.32 mL of the reaction mixture to 0.8 mL of a titanium reagent, and the yellow color, produced by reacting hydrogen peroxide formed by the enzyme reaction and the titanium reagent, was measured by measuring the absorbance at 410 nm ($A_{410}$) as an index. Separately, the enzyme solution was added to the substrate solution, and the resulting mixture is immediately mixed with the titanium reagent. The resulting mixture was similarly measured its color and the value was used as the value at the reaction zero minutes. Then, the amount of the formed hydrogen peroxide is determined and the PVA-oxidizing activity is calculated based on the following formula. It is known that the absorbance at 410 nm ($A_{410}$) increases by "1" when 3.65 μmole/mL of hydrogen peroxide is formed. Therefore, in the following Formula 1, the coefficient of "3.65" has been multiplied. One unit of the PVA-oxidizing activity is defined as the amount of enzyme that forms 1 μmole of hydrogen peroxide per min under the above conditions. Titanium reagent is prepared by diluting 5% titanium sulfate (IV) solution, commercialized by Nacalai Tesque Inc., Kyoto, Japan, 25-fold with 10% (w/w) sulfuric acid.

$$\text{PVA-oxidizing act.} = \left( A_{410}^{60\text{ min}} - A_{410}^{0\text{ min}} \right) \times 3.65 \times 1/0.5 \times 1/60 \times \text{dilution rate } (U/\text{mL}) \quad \text{Formula 1}$$

As shown in the above (2), the PVA-degrading enzyme of the present invention has an activity of hydrolyzing β-diketone, i.e., β-diketone-hydrolyzing activity. Enzymes having β-diketone-hydrolyzing activity can hydrolyze an oxidized PVA having a β-diketone structure (i.e., oxidized PVA). Beta-diketone-hydrolyzing activity can be detected by examining the activity of hydrolyzing 2, 4-pentanedione which is a model compound of oxidized PVA having a β-diketone structure. Acetone and acetic acid are formed when a PVA-degrading enzyme hydrolyzes 2,4-pentanedione. Therefore, for example, β-diketone-hydrolyzing activity can be detected by the following method using 2,4-pentanedione as a substrate.

<Detection of β-Diketone Hydrolyzing Activity>

2,4-Pentanedione (Reagent grade, commercialized by Wako Pure Chemical Industries Co., Ltd., Osaka, Japan) was added to 50 mM sodium phosphate buffer (pH 7.0) to give a concentration of 0.2% (w/v) to make into a substrate solution. To 1 mL of the substrate solution, 0.2 mL of enzyme solution and 0.8 mL of 50 mM sodium phosphate buffer (pH 7.0) were added and then the mixture was shaken at 27° C. for 3 hours for the reaction. After the reaction, 2 mL of the reaction mixture was withdrawn and put in a glass vial, and then the vial was sealed and heated at 95° C. for 40 min. Successively, 1 mL of gas in the vial was collected and subjected to the following gas chromatography analysis to detect acetone, a hydrolysis product of 2,4-pentanedione. The enzyme solution which produced acetone by the method was judged to be "an enzyme having β-diketone hydrolyzing activity".

<Conditions for Gas Chromatography (GC)>

| Equipment: "GC-2010 Plus" (manufactured by Shimadzu Corporation, Kyoto, Japan) Column: "DB-5" (Part number. 122-5032) (manufactured by Agilent Technologies Japan, Ltd., Tokyo, Japan) | |
|---|---|
| Temperature of vaporization chamber: 150° C.; | Injection mode: split; Carrier gas: Helium; |
| Control mode: linear velocity; Total flow rate: 12.6 mL/min; | Pressure: 114.6 kPa; Column flow rate: 1.6 mL/min; |
| Line speed: 35. 0 cm/sec; Split ratio: 5.0; | Purge flow rate: 3.0 mL/min; |
| Column temperature: 40° C.; Column temperature program: After keeping the column temperature at 40° C. for 5 min, the column was heated to 100° C. at 5° C./min over 12 min, then the column temperature was raised to 250° C. at 10° C./min over 15 min, and kept at 250° C. for 3 min. | Equilibrium time: 1.0 min; |
| Detector: FID; | Detector temperature: 260° C.; |

The PVA-degrading enzyme of the present invention acts solely as a PVA-degrading enzyme exhibiting PVA-degrading activity, by having the above-mentioned PVA-oxidizing activity (characteristic (1)) and β-diketone-hydrolyzing activity (characteristic (2)). While, activity as a PVA-degrading enzyme can be measured, for example, by measuring the viscosity reduction of a PVA solution, caused by the degradation of PVA, as an index using the following method.

<Method for Measuring PVA-Degrading (Viscosity-Reducing) Activity>

To 0.5 mL of a substrate solution prepared by dissolving PVA (Reagent grade polyvinyl alcohol, polymerization degree: 2,000, Nacalai Tesque Inc., Kyoto, Japan) into 100 mM sodium phosphate buffer (pH 7.0) to give a concentration of 2% (w/v), 15 μL of 2% (w/v) of sodium azide solution was added, and then 0.5 mL of an enzyme solution is further added and reacted with shaking at 27° C. for 60 min. After the reaction, 0.6 mL of the reaction mixture was withdrawn and its viscosity was measured using a Cone plate-type viscometer ("DV-II+Pro", Brookfield Co., Ltd.) at 30° C. Separately, the enzyme solution was added to the substrate solution and the viscosity was measured immediately, and the viscosity was used as that at zero-min reaction. The PVA-degrading activity was calculated based on the following formula. One unit of the PVA-degrading activity was defined as the amount of enzyme that causes a 10%-reduction of relative viscosity per min under the above conditions.

PVA-degrading act.=Relative viscosity reducing rate (%)×1/10×1/0.5×1/60×dilution rate (U/mL)

$$\text{Relative viscosity reducing rate (\%)} = \{(V_0 - V_{60})/(V_0 - V_w)\} \times 100 \quad \text{Formula 2:}$$

$V_0$: Viscosity at 0-time reaction
$V_{60}$: Viscosity at 60-min reaction
$V_w$: Viscosity of water Furthermore, PVA-degrading enzyme of the present invention usually has a characteristic shown in the above (3), i.e., a characteristic of exhibiting the molecular weight of 100,000±20,000 in SDS-polyacrylamide gel electrophoresis (SDS-PAGE).

In a preferred embodiment, PVA-degrading enzyme of the present invention shows the following enzymatic properties (4) to (7) with regard to the PVA-oxidizing activity:

(4) Optimum temperature:
   35 to 40° C. under the conditions of 60 min-reaction at pH 7.0;
(5) Optimum pH
   pH 6.5 to 8.0 under the conditions of 60 min-reaction at 27° C.;
(6) Thermal stability:
   Stable up to 45° C. under the conditions of holding at pH 7.0 for 60 min; and
(7) pH stability:
   Stable in a range of pH 4.5 to 10.5 under the conditions of holding at 4° C. for 24 hours:

Furthermore, in a more preferred embodiment, the PVA-degrading enzyme of the present invention includes enzymes having the following characteristic (8):

(8) having the amino acid sequence of SEQ ID NO: 1 as N-terminal amino acid sequence.

The PVA-degrading enzyme of the present invention usually has a prescribed amino acid sequence as a polypeptide, and preferred examples thereof include the amino acid sequence of SEQ ID NO: 2 or SEQ ID NO: 3, or those homologous to them. The enzyme having a homologous amino acid sequence to SEQ ID NO: 2 or SEQ ID NO: 3 includes that having an amino acid sequence where one or more amino acids in SEQ ID NO: 2 or SEQ ID NO: 3 are deleted, replaced, or added with holding the activity of oxidizing PVA to form hydrogen peroxide and the activity of hydrolyzing □-diketone. Enzymes having amino acid sequences having homology (sequence identity) of, usually 84% or higher, preferably, 90% or higher, more preferably, 95% or higher, to SEQ ID NO: 2 or SEQ ID NO: 3 are preferably used.

As described later in the section of Experiments, the amino acid sequences of SEQ ID NO: 2 and SEQ ID NO: 3, exemplified as the amino acid sequence of the PVA-degrading enzyme of the present invention, have a characteristic structure that a region showing a homology to the conventionally known PVA dehydrogenase is present in the N-terminal first half, and a region showing a homology to the conventionally known oxidized PVA hydrolase is present in the C-terminal late half. The finding that PVA-degrading enzyme of the present invention possesses such characteristic amino acid sequences suggests the possibility that it oxidizes PVA at the N-terminal first half of the polypeptide and hydrolyzes oxidized PVA at the C-terminal late half of the polypeptide as a hybrid enzyme.

As described later in the section of Experiments, a PVA-oxidizing enzyme fragment derived from the N-terminal first half of the polypeptide and an oxidized PVA-hydrolyzing enzyme fragments derived from the C-terminal late half of the polypeptide were actually observed in the culture of *Pseudomonas* sp. VT1B strain. From the results, it was demonstrated that the enzyme functions as a hybrid enzyme and PVA-oxidizing enzyme and oxidized PVA-hydrolyzing enzyme are present at the N-terminal first half and the C-terminal late half of the polypeptide, respectively. This finding indicates that a PVA-oxidizing enzyme and an oxidized PVA-hydrolyzing enzyme can be separately prepared by artificial limited-proteolysis using a protease and the like, if necessary.

Although the PVA-degrading enzyme of the present invention is not restricted by the source, microorganisms belonging to the genus *Pseudomonas* can be used as a preferred source, and *Pseudomonas* sp. VT1B strain, found by the present inventors, or mutant strains thereof can be suitably used.

The DNA of the present invention means that having a nucleotide sequence encoding the amino acid sequence of the PVA-degrading enzyme of the present invention described above. As the DNA of the present invention, that from natural origin and that artificially synthesized can be used as long as it has a nucleotide sequence encoding the amino acid sequence of the PVA-degrading enzyme of the present invention. For example, the natural source of the DNA includes microorganisms of the genus *Pseudomonas* containing *Pseudomonas* sp. VT1B strains, and the genomic DNA containing the DNA of the present invention can be obtained from these cells. The genomic DNA containing the DNA of the present invention can be obtained by the steps of inoculating such microorganisms to nutrient medium, culturing about 5 to 10 days under aerobic conditions, collecting cells from the culture, and treating the cells by cell wall-lysis enzymes such as lysozyme and □-glucanases or by ultrasonication to elute the genomic DNA from the cells. In such case, protein-hydrolyzing enzymes such as proteases may be used in combination, or a surfactant such as SDS may be allowed to co-exist, or it may be frozen and thawed. The objective genomic DNA can be obtained by applying conventional methods such as for example, phenol extraction, alcohol precipitation, centrifugation, ribonuclease treatment on the resulting treated product. To artificially synthesize the DNA of the present invention, for example, the DNA can be chemically synthesized based on the amino acid sequence of SEQ ID NO: 2 or SEQ ID NO: 3. Further, the DNA can be advantageously synthesized by PCR using a chemically synthesized DNA as a suitable primer and the genomic DNA containing the DNA as a template.

The DNA of the present invention usually has a prescribed nucleotide sequence, and preferred examples thereof include the nucleotide sequence of SEQ ID NO: 4 or SEQ ID NO: 5, homologous nucleotide sequences thereof, and complement nucleotide sequences thereof. The DNA having a homologous nucleotide sequence to SEQ ID NO: 4 or SEQ ID NO: 5 includes that having a nucleotide sequence where one or more nucleotides in SEQ ID NO: 4 or SEQ ID NO: 5 are deleted, replaced, or added with holding the encoding PVA-degrading activity. DNAs having a nucleotide sequence having homology (sequence identity) of, usually 82% or higher, preferably, 85% or higher, more preferably, 90% or higher, by far more preferably, 95% or higher, to SEQ ID NO: 4 or SEQ ID NO: 5 are preferably used. In the DNA encoding these PVA-degrading enzymes, the DNA of the present invention also includes that having a nucleotide sequence where one or more nucleotides are replaced with other nucleotide without altering the encoded amino acid sequence of PVA-degrading enzyme, based on the degeneracy of the genetic code.

A recombinant DNA can be advantageously obtained by inserting the DNA of the present invention into an appropriate autonomously replicable vector. A recombinant DNA is usually composed of a DNA and an autonomously replicable vector, and if a DNA can be obtained, it can be easily prepared by conventional recombinant DNA techniques. As examples of such vectors, plasmids, phage or cosmid vectors, etc., can be used and appropriately selected depending on the host cell to be introduced or the introduction method. Types of vectors are not specifically restricted, and that possible to be expressed in a host cell can be appropriately selected. Depending on the type of host cell, a promoter sequence can be appropriately selected to express the gene, and a vector constructed by incorporating the promoter sequence and the gene into various plasmids can be used as the expression vectors. As such expression vectors, for example, phage vectors, plasmid vectors, viral vectors, retroviral vectors, chromosome vectors, episomal vectors and virus-derived vectors (e.g., bacterial plasmid, bacteriophage, yeast episomes, yeast chromosome elements) and viruses (e.g., baculovirus, papovavirus, vaccinia virus, adenovirus, tripox virus, pseudorabies virus, herpes virus, lentivirus and retrovirus) and vectors derived from their combinations (e.g., cosmid and phagemid) are available.

Preferred vectors for use in bacteria include, for example, pQE-70, pQE-60, pBS vectors, Phargescript vectors, Bluescript vectors, pNH8A, pNH6a, pNH18A and pNH46A; and ptrc99a, pKK223-3, pKK233-3, pDR540, pRIT5, and the like. Preferred vectors for use in eukaryotic organisms include, for example, pWLNE0, pSV2CAT, pOG44, pXT1 and pSG; and pSVK3, pBPV, pMSG, pSVL and the like.

To insert the DNA of the present invention into such vectors, conventional methods used in the field are usually employed. Specifically, the gene DNA containing the objective DNA and an autonomously replicable vector are firstly cleaved by restriction enzymes and/or ultrasonication, then the formed DNA fragment and the vector fragment are ligated. A recombinant DNA thus obtained can be replicated infinitely by the steps of introducing it into an appropriate host and culturing the resulting transformant.

The recombinant DNA, thus obtained, can be introduced into an appropriate host microorganism including *E. coli*, *Bacillus subtilis*, Actinomycetes, yeast, etc. To obtain a transformant, a colony hybridization method can be applied. Also, a transformant can be selected by the steps of culturing the microorganism in nutrient medium and detecting the transformant producing the PVA-degrading enzyme.

The PVA-degrading enzyme of the present invention has both PVA-oxidizing activity and oxidized PVA-hydrolyzing activity. Further, as described later in the section of Experiments, the enzyme has a region showing homology, albeit low, with the amino acid sequence of the conventional PVA dehydrogenase at the N-terminal first half of the amino acid sequence of the polypeptide. The enzyme also has a region showing relatively high homology with the amino acid sequence of the conventional oxidized PVA hydrolase at the C-terminal late half of the amino acid sequence of the polypeptide. Based on this finding, a DNA encoding only the amino acid sequence of the N-terminal first half of the PVA-degrading enzyme can be artificially created by inserting a termination codon, a terminator sequence and the like into the middle part of the DNA of the present invention, i.e., the DNA encoding the PVA-degrading enzyme of the present invention. Also, a polypeptide (enzyme) having only PVA-oxidizing activity can be created by allowing to express the resulting modified gene in an appropriate host microorganism using recombinant DNA technology. The resulting polypeptide can be produced and used as a recombinant PVA-oxidizing enzyme.

As described later in the section of Experiments, those amino acid sequences of SEQ ID NO: 2 and SEQ ID NO: 3, exemplified as the amino acid sequence of the PVA-degrading enzyme of the present invention, showed about 84% homology (sequence identity) in the whole amino acid sequence. However, when limited to the region of the amino acid sequence consisting of about 450 amino acid residues at the N-terminal first half, having homology with the amino acid sequence of a conventional PVA dehydrogenase, their homology (sequence identity) is about 90%. Therefore, as the enzyme having only PVA-oxidizing activity created in the above, the enzyme having an amino acid sequence consisting of about 450 amino acid residues at the N-terminal first half of SEQ ID NO: 2 or SEQ ID NO: 3, or, a mutant enzyme having an amino acid sequence that one or more amino acid residues in the amino acid sequence is deleted, replaced, or added in a range of holding the homology (sequence identity) of about 90%, can be used.

While, based on the findings described above, a DNA encoding only the amino acid sequence of the C-terminal late half of the PVA-degrading enzyme can be artificially created by inserting a promotor sequence, initiation codon, nucleotide sequence encoding the secretory signal sequence and the like into the middle part of the DNA of the present invention, i.e., the DNA encoding the PVA-degrading enzyme of the present invention. Also, a polypeptide (enzyme) having only oxidized PVA-hydrolyzing activity can be created by allowing to express the resulting modified gene by the same manner described above, and the resulting polypeptide can be used as a recombinant oxidized PVA-hydrolyzing enzyme.

Further, as described above, those amino acid sequences of SEQ ID NO: 2 and SEQ ID NO: 3, exemplified as the amino acid sequence of the PVA-degrading enzyme of the present invention, showed about 84% homology (sequence identity) in the whole amino acid sequence. However, when limited to the region of the amino acid sequence consisting of about 340 amino acid residues at the C-terminal late half, having homology with the amino acid sequence of a conventional oxidized PVA hydrolase, their homology (sequence identity) is about 85%. Therefore, as the enzyme having only oxidized PVA-hydrolyzing activity created in the above, the enzyme having an amino acid sequence consisting of about 340 amino acid residues at the C-terminal late half of SEQ ID NO: 2 or SEQ ID NO: 3, or, a mutant enzyme having an amino acid sequence that one or more amino acid residues in the amino acid sequence is deleted, replaced, or added in a range of holding the homology (sequence identity) of about 85%, can be used.

Furthermore, both amino acid sequences of SEQ ID NO: 2 and SEQ ID NO: 3, exemplified as the amino acid sequence of the PVA-degrading enzyme of the present invention, have amino acid sequences consisting of about 90 to 100 amino acid residues as a linker unit between the region at the N-terminal first half, showing a homology to the amino acid sequence of PVA dehydrogenase, and the region at the C-terminal late half, showing a homology to the amino acid sequence of oxidized PVA hydrolase. If the PVA-degrading enzyme of the present invention has a function of PVA-oxidizing enzyme only in the N-terminal first half and a function of oxidized PVA-hydrolyzing enzyme in only the C-terminal late half, it was considered that the linker plays a role for constructing hybrid enzyme without adversely affecting the both activity. Not only the case of PVA-degrading enzyme of the present invention, there is a possibility that the linker unit can be used to connect the two other appropriate enzymes to create a hybrid enzyme.

A nutrient medium used for culturing the microorganism capable of producing the PVA-degrading enzyme of the present invention (including transformants) is not restricted to the specific one as far as it can be used for the growth by the microorganisms and for producing the PVA-degrading enzyme, and both synthetic medium and natural medium can be used. Any carbon source can be used as far as it can be used for the growth by the microorganism, and includes, for example, polyalcohols such as glycerin, ethylene glycol, PVA, and the like; saccharides such as starch and phytoglycogen derived from plants, glycogen and pullulan derived from animals and microorganisms, or these partial degradation products, glucose, fructose, lactose, sucrose, mannitol, sorbitol, molasses and the like; organic acids such as citric acid, succinic acid, and the like. The concentration of these carbon sources in the medium can be appropriately selected depending on the type of carbon source. Any nitrogen source, for example, inorganic nitrogen compounds such as ammonium salts, nitrates, and the like, organic nitrogen-containing materials such as urea, corn steep liquor, casein, peptone, yeast extract, meat extract, and the like, can be appropriately used. As inorganic components, for example, salts such as calcium salts, magnesium salts, potassium salts, sodium salts, phosphates, manganese salts, zinc salts, iron salts, copper salts, molybdenum salts, cobalt salts, and the like can be appropriately used. Furthermore, if necessary, amino acids, vitamins and the like can be appropriately used.

The cultivation of microorganisms can be carried out under aerobic conditions, usually, in a range of 15 to 37° C. and at pH 5.5 to 10, preferably, in a range of 20 to 34° C. and at pH 5.5 to 8.5. Culturing time is not restricted as far as the microorganism can proliferate, preferably, 5 days to 10 days. Further, the dissolved oxygen concentration of the culture fluid in the culture conditions is not restricted to the specific one, but usually in a range of 0.5 to 20 ppm is preferable. For controlling the concentration, means such as adjustment of ventilation volume and stirring can be appropriately carried out. In addition, batch culture and continuous culture are appropriately selected as the cultivation method.

After culturing the microorganism as described above, the culture fluid containing the PVA-degrading enzyme of the present invention is collected. Since the activity of PVA-degrading enzyme can be detected in the culture supernatant obtained by removing the cells from the culture, the culture supernatant can be collected as a crude enzyme preparation, and also, the whole culture fluid can be used as a crude enzyme preparation. To remove cells from the culture fluid, conventionally known solid-liquid separation methods are employed. For example, a method of centrifuging the culture fluid, or a method of separating cells by filtration using a pre-coated filter, a method of separating cells by membrane filtration using a flat membrane or a hollow fiber membrane, are appropriately used. Although the culture supernatant can be used as a crude enzyme solution, it is usually used after the concentration. As a concentration method, salting out using ammonium sulfate, precipitation using acetone or alcohol, and membrane concentration using a flat membrane or a hollow fiber membrane, can be used.

As described above, the crude enzyme solution can be used intact or after the concentration as the PVA-degrading enzyme of the present invention. If necessary, the crude enzyme can be used after separating and purifying it by the conventional methods. For example, as described later in the section of Experiments, the PVA-degrading enzyme can be obtained as an enzyme purified to a level showing a single band in electrophoresis by the steps of concentrating the culture fluid by salting out, dialyzing the resulting partially purified enzyme, purifying by anion exchange column chromatography using "DEAE-TOYOPEARL 650S", and purifying by cation exchange column chromatography using "CM-TOYOPEARL 650S". Further, for purifying the PVA-degrading enzyme, appropriate purification methods such as hydrophobic column chromatography, gel filtration column chromatography, affinity column chromatography, and preparative isoelectric point electrophoresis can be advantageously used.

In the case of the PVA-degrading enzyme being a recombinant enzyme, it may accumulate in the cell depending on the type of host. In such a case, cells or culture can be used intact. However, if necessary, the accumulated enzyme can be advantageously used after a step of extracting from the cells by using osmotic shock or surfactant, or after disrupting the cells by ultrasonic or cell-lysis enzyme, and separating the recombinant enzyme from the cells and its debris by filtration or centrifugation.

PVA as a substrate of the PVA-degrading enzyme of the present invention is not specifically restricted by the molecular weight (or the degree of polymerization) and the degree of saponification. Usually, PVA having the molecular weight of 15,000 to 200,000 (the degree of polymerization of 400 to 3900) and the degree of saponification of 70 to 99 mol % can be used.

In the case of allowing the PVA-degrading enzyme of the present invention to act on PVA as a substrate, the substrate concentration is not restricted to the specific one. For example, the reaction of the PVA-degrading enzyme of the present invention proceeds and degrades PVA even in the case of using a relatively low substrate concentration of 0.1% (w/v). In an industrial level, substrate concentrations of 1% (w/v) or higher is preferable and PVA can be advantageously degraded under this condition. The reaction temperature is controlled to a temperature at which the reaction proceeds, i.e., up to 55° C., preferably, 25 to 50° C.

The reaction pH is adjusted to, usually, in a range of pH 4.5 to 8.0, preferably, pH 5.0 to 7.0. Since the amount of enzyme used and the reaction time are closely related, they can be appropriately selected by the progress of the objective enzymatic reaction.

Following experiments explain the present invention in detail.

<Experiment 1: Cultivation of *Pseudomonas* sp. VT1B Strain (NBRC110478) and Preparation of Crude Enzyme>

A liquid culture medium containing 1 g/L of PVA (Reagent grade polyvinyl alcohol, polymerization degree: 500, commercialized by Nacalai Tesque Inc., Kyoto, Japan), 0.3 g/L of dipotassium phosphate, 1 g/L of potassium phosphate, 0.5 g/L of sodium chloride, 1 g/L of ammonium nitrate and water was adjusted to pH 7.0 and sterilized by autoclaving at 121° C. for 20 min. To the sterilized medium, magnesium sulfate 7 hydrate, calcium chloride 2 hydrate and ferric sulfate 7 hydrate, each of which was sterilized by filtering, were added to give final concentrations of 0.5 g/L, 0.05 g/L, and 0.02 g/L, respectively. Further, to the resulting medium, thiamine hydrochloride and pyrroloquinoline quinone (PQQ), each of which was sterilized by filtering, were added to give final concentrations of 0.01 g/L and 10 □g/L, respectively. The resulting liquid culture medium was used for cultivation.

*Pseudomonas* sp. VT1B strain (NBRC110478) subcultured on an agar plate was scraped with a platinum wire and suspended in about 2 mL of sterilized 0.85% (w/v) sodium chloride aqueous solution. Turbidity (absorbance at 660 nm, $A_{660}$) of the suspension was adjusted to 0.5, and 60 DL of the suspension was inoculated into a test tube containing 3 mL of the liquid medium, and then cultured by shaking at 240 rpm at 27° C. for 5 days to make into a seed culture.

To 20 Erlenmeyer flasks with a 500 mL-volume, 200 mL each of the same liquid medium described above, except for further adding a deforming agent (ADEKANOL LG-126) to give a final concentration of 0.2 g/L, was dispensed. Then, the seed culture obtained above was inoculated to each liquid culture medium to give a concentration of 2% (v/v) and cultured by shaking at 240 rpm at 27° C. for 10 days to make into main culture. After the cultivation, the culture was centrifuged at 8,000 rpm for 20 min to remove cells and about 4 L of culture supernatant was obtained as a crude enzyme solution. PVA-oxidizing activity of the crude enzyme solution was about 139 units as the total activity.

<Experiment 2: Purification of PVA-Degrading Enzymes>

Ammonium sulfate was added to 4 L of the culture supernatant obtained in Experiment 1 to give a final concentration of 60%-saturation and the resulting solution was stood at 4° C. for 24 hours for salting out. The formed salting-out precipitate was collected by centrifuging at 11,000 rpm for 30 min, dissolved in 10 mM phosphate buffer (pH 7.0), and dialyzed against the same buffer, and about 45 mL of ammonium sulfate salting-out dialysis solution was obtained. The ammonium sulfate salting out dialysis solution was subjected to anion exchange column chromatography using "DEAE-TOYOPEARL 650S" gel (commercialized by Tosoh Corporation, Tokyo, Japan) (gel volume: 24 mL). PVA-oxidizing activity was separated to the active fraction eluted in the non-adsorption fraction without adsorbing to the column equilibrated to 10 mM phosphate buffer (pH 7.0) and the active fraction adsorbed to the column and eluted with a linear gradient of NaCl from zero to 5M. The active fraction, adsorbed to "DEAE-TOYOPE-ARL 650S" gel and eluted by NaCl, was dialyzed against 10 mM phosphate buffer (pH 7.0) and collected as a purified preparation of PVA-degrading enzyme (PVA-B).

Then, the active fraction, not adsorbed to the anion exchange column using "DEAE-TOYOPEARL 650S", was subjected to cation exchange column chromatography using "CM-TOYOPEARL 650S" gel (commercialized by Tosoh Corporation, Tokyo, Japan) (gel volume: 23 mL). The PVA-oxidizing activity was adsorbed on "CM-TOYOPEARL 650S" gel, and then, eluted at 0.08 M NaCl concentration within a linear gradient of NaCl from zero to 0.5 M. The active fraction was collected, dialyzed against 10 mM phosphate buffer (pH 7.0), and collected as a purified preparation of PVA-degrading enzyme (PVA-A).

Total activity as PVA-oxidizing activity, total protein, specific activity, and yield of the PVA-degrading enzyme at each purification step were summarized in Table 1. Further, 2,4-pentanedione-degrading activities detected qualitatively for the culture supernatant (crude enzyme) and the purified enzyme preparation were also shown in Table 1. In addition, PVA-degrading activities measured at each purification step as in the case of PVA-oxidizing activity were also shown in Table 1. In Table 1, the notation "Yes" for 2, 4-pentanedione-degrading activity means that acetone, a hydrolysis product of 2, 4-pentanedione, has been detected.

Figure 2:
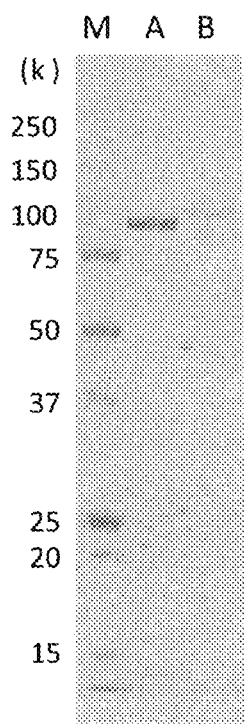
FIG. 2 is a SDS-polyacrylamide gel electrophoresis pattern of purified preparation of PVA-degrading enzyme.

("Precision Plus protein uncolored standard", commercialized by Bio-Rad Laboratories Inc., Tokyo, Japan) subjected to the electrophoresis at the same time. The results are shown in FIG. 2. In FIG. 2, symbol "M" means the molecular weight marker subjected to the electrophoresis at the same time, and symbols "A" and "B" mean PVA-A and PVA-B, respectively. As shown in FIG. 2, both PVA-A and PVA-B showed almost a single protein band, and in comparison with the molecular weight markers, it was revealed that PVA-A and PVA-B have approximately the same molecular weight of 100,000±20,000.

<Experiment 3-2: Optimum Temperature and Optimum pH>

Figure 3:
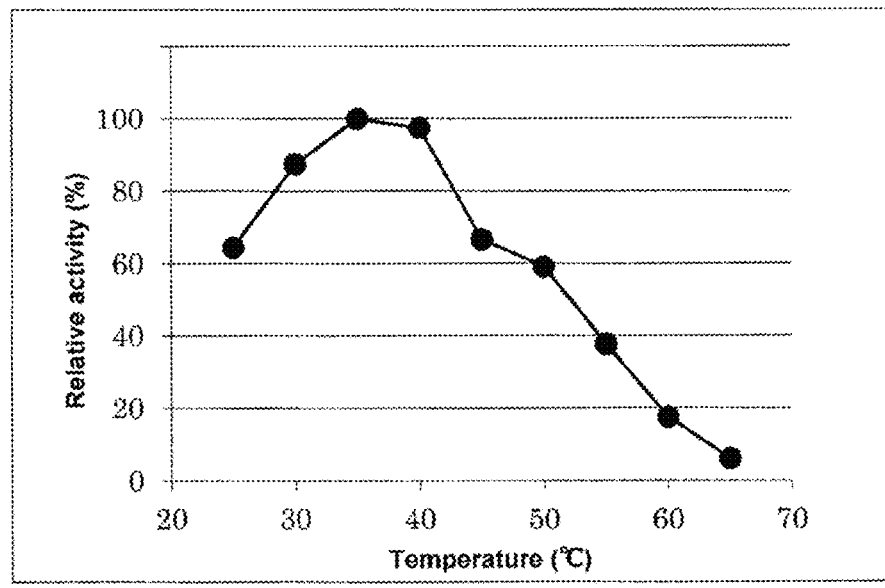
FIG. 3 is a graph showing the optimum temperature of PVA-oxidizing activity of the purified preparation of a PVA-degrading enzyme, PVA-A.
Figure 4:
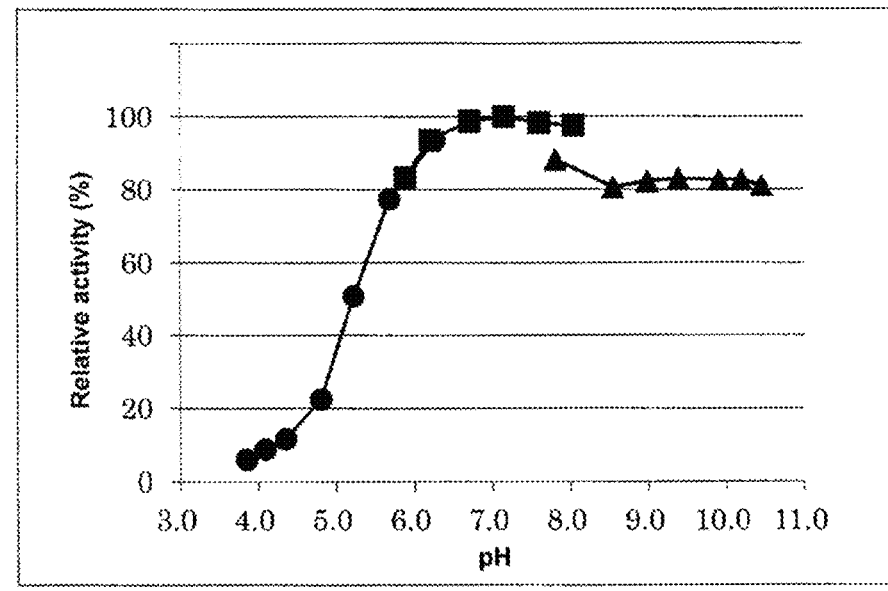
FIG. 4 is a graph showing the optimum pH of PVA-oxidizing activity of the purified preparation of a PVA-degrading enzyme, PVA-A.

In the two purified preparations of the PVA-degrading enzyme, PVA-A was used for investigating effects of temperature and pH on the activity using PVA-oxidizing activity as an index according to the assay method. These results were shown in FIG. 3 (optimum temperature) and FIG. 4 (optimum pH). In FIG. 4, symbols, "●", "■" and "▲", mean values measured by using acetate buffer, phosphate buffer and glycine-NaOH buffer, respectively, for pH control. It was revealed that the optimum temperature of PVA-oxidizing activity is 35 to 40° C. under the conditions of 60

TABLE 1

| Purification step | Total Activity (U) | Total Protein (mg) | Relative Activity (U/mg) | Yield (%) | 2,4-Pentanedione -Degrading Activity | Total PVA-Degrading Activity (Viscosity-reducing Activity) (U) |
|---|---|---|---|---|---|---|
| Culture supernatant (Crude enzyme) | 139.1 | 68.1 | 2.0 | 100 | Yes* | —** |
| 60%-Saturated Ammonium Sulfate Precipitation and Dialysis | 116.9 | 57.2 | 2.0 | 84.0 | —** | 190 |
| Non-adsorbed fraction of Anion exchange Chromatography | 22.1 | 12.8 | 1.7 | 15.9 | —** | 37.2 |
| Purified preparation, PVA-B, obtained by Anion exchange Chromatography | 3.3 | 1.7 | 1.9 | 2.4 | Yes* | 8.4 |
| Purified preparation, PVA-A, obtained by Cation exchange Chromatography | 5.4 | 1.7 | 3.2 | 3.9 | Yes* | 8.2 |

*Acetone, a product by the hydrolysis, was qualitatively detected.
**Not measured.

As shown in Table 1, two types of purified enzyme preparations, "PVA-A" and "PVA-B", having any of PVA-oxidizing activity, which is the activity to oxidize PVA and form hydrogen peroxide; 2,4-pentanedione (one of □-diketone)-hydrolyzing activity; and PVA-degrading (viscosity-reducing) activity, were obtained.

To determine the purities, each of the PVA-A and PVA-B as purified enzyme preparations of PVA-degrading enzyme was subjected to SDS-polyacrylamide gel electrophoresis (SDS-PAGE) (8 to 16 w/v % concentration gradient). Since both preparations showed a single protein band, it was revealed that they were highly purified preparations.

<Experiment 3: Properties of PVA-Degrading Enzymes>
<Experiment 3-1: Molecular Weight>

Purified PVA-degrading enzyme preparations obtained in Experiment 2, i.e., PVA-A and PVA-B, were subjected to SDS-polyacrylamide gel electrophoresis (8 to 16 w/v % concentration gradient), and their molecular weights were measured by comparing with the molecular weight markers min-reaction at pH 7.0, and the optimum pH is pH 6.5 to 8.0 under the condition of 60 min-reaction at 27° C. Although the detailed data is omitted, PVA-B showed almost the same optimum temperature and optimum pH with those of PVA-A.

<Experiment 3-3: Thermal Stability and pH Stability>

Figure 5:
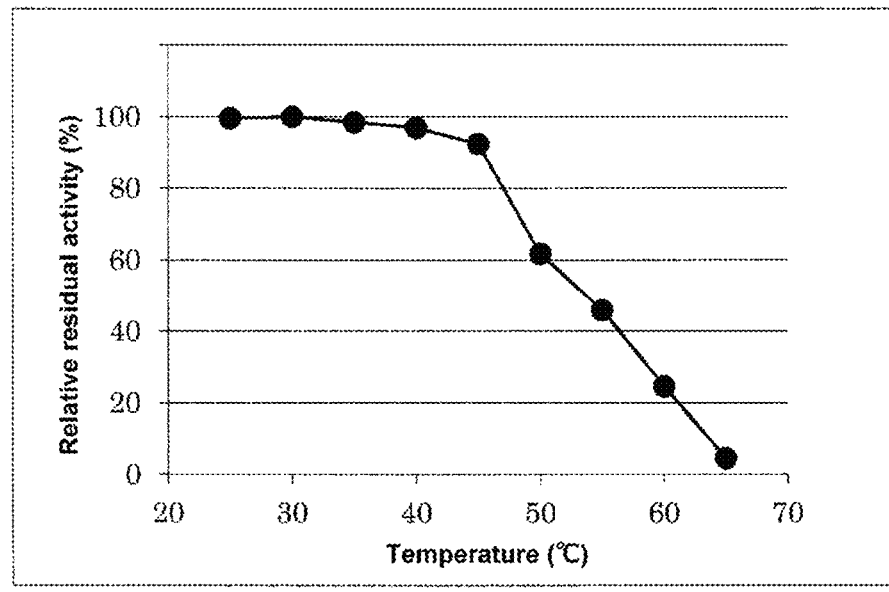
FIG. 5 is a graph showing the thermal stability of PVA-oxidizing activity of the purified preparation of a PVA-degrading enzyme, PVA-A.
Figure 6:
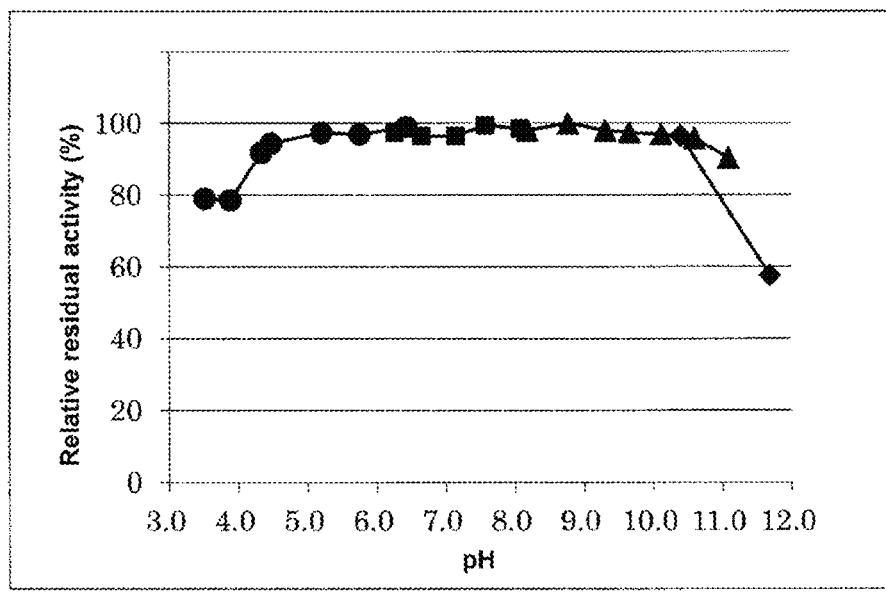
FIG. 6 is a graph showing the pH stability of PVA-oxidizing activity of the purified preparation a PVA-degrading enzyme, PVA-A.

In the two purified preparations of the PVA-degrading enzyme, PVA-A was used for investigating thermal stability and pH stability using PVA-oxidizing activity as an index according to the assay method. Thermal stability was determined by the steps of incubating the enzyme solution (in 10 mM phosphate buffer, pH 7.0) at various temperature for 60 min, cooling in water, and then measuring the residual enzyme activity. pH Stability was determined by the steps of incubating the enzyme solution in 100 mM buffer with different pH at 4° C. for 24 hours, adjusting pH to 7.0, and then measuring the residual enzyme activity. These results are shown in FIG. 5 (thermal stability) and FIG. 6 (pH stability), respectively. In FIG. 6, symbols, "●", "■", "▲"

and "♦", mean values measured by using acetate buffer, phosphate buffer, glycine-NaOH buffer, and potassium chloride-NaOH buffer, respectively, for pH control. As is evident from FIG. 5, it was revealed that PVA-oxidizing activity is stable up to 45° C. Also, as is evident from FIG. 6, it was revealed that PVA-oxidizing activity is stable in a range of pH 4.5 to 10.5. Although the detailed data is omitted, PVA-B showed almost the same thermal stability and pH stability with those of PVA-A.

<Experiment 3-4: Effects of Various Metal Salts on PVA-Oxidizing Activity>

Using the purified enzyme preparations of PVA-A and PVA-B, obtained by the method of Experiment 2, effects of various metal salts on the enzyme activity were investigated according to the assay of the PVA-oxidizing activity as an index in the presence of 1 mM metal salts. The results are shown in Table 2.

TABLE 2

| Metal salt | Relative activity (%) | |
|---|---|---|
| | PVA-A | PVA-B |
| None | 100 | 100 |
| AlCl₃ | 91 | 63 |
| CaCl₂ | 98 | 98 |
| CoCl₂ | ---* | ---* |
| CuCl₂ | ---* | ---* |
| FeCl₂ | ---* | ---* |
| FeCl₃ | 29 | 19 |
| HgCl₂ | 22 | 4 |
| KCl | 93 | 116 |
| MgCl₂ | 98 | 104 |
| MnCl₂ | 96 | 87 |
| NaCl | 94 | 106 |
| NiCl₂ | 91 | 76 |
| PbCl₂ | ---** | ---** |
| RbCl₂ | 91 | 99 |
| SnCl₂ | 78 | 102 |
| SrCl₂ | 99 | 101 |
| EDTA | 56 | 45 |

---*: Could not be measured by the fading in color caused by reacting with the reaction product.
---**: Could not be measured by the formation of precipitates.

As shown in Table 2, a significant difference was not observed between PVA-A and PVA-B in the effects of the metal salt on PVA-oxidizing activity, and it was revealed that the activity was remarkably inhibited by $Hg^{2+}$ and $Fe^{3+}$ ions, and also inhibited by EDTA.

<Experiment 3-5: Substrate Specificity of PVA-Oxidizing Activity>

The substrate specificity of PVA-oxidizing activity was investigated by allowing PVA-A and PVA-B, the purified enzyme preparations obtained by the method in Experiment 2, to act on various secondary alcohols, primary alcohols and the like as substrates. In other words, the PVA-oxidizing activity of the enzymes was measured for primary alcohols having different chain length (methanol, ethanol, propanol, butanol, pentanol, hexanol, heptanol, and decanol), secondary alcohols (2-propanol, 2-pentanol, 2-hexanol, 4-heptanol, 2-octanol, 4-decanol, and 2, 4-pentanediol), and a tertiary alcohol (tert-butanol). Substrate concentration was set to 1% (v/v), and those that did not dissolve in water were suspended to be a saturated concentration. The results are shown in Table 3.

TABLE 3

| Substrate | Relative activity (%) | |
|---|---|---|
| | PVA-A | PVA-B |
| PVA | 100 | 100 |
| 2-Propanol | 0 | 1 |
| 2-Pentanol | 2 | 5 |
| 2-Hexanol | 5 | 8 |
| 4-Heptanol | 21 | 12 |
| 2-Octanol | 3 | 6 |
| 4-Decanol | 3 | 1 |
| Methanol | 0 | 0 |
| Ethanol | 0 | 0 |
| Propanol | 0 | 0 |
| Butanol | 0 | 0 |
| Pentanol | 0 | 0 |
| Hexanol | 0 | 1 |
| Heptanol | 0 | 1 |
| Decanol | 0 | 0 |
| 2,4-Pentanediol | 0 | 0 |
| tert-Butanol | 0 | 1 |

As shown in Table 3, PVA-A and PVA-B weakly acted on 4-heptanol as a secondary alcohol with relative activity of 12 to 21%, where the PVA-oxidizing activity against PVA was regarded as 100%. The enzymes slightly acted on 2-hexanol and 2-octanol as other secondary alcohols with the relative activity of 3 to 8%. However, the enzymes hardly acted on the other secondary alcohols, primary alcohols, tertiary alcohol (tert-butanol), and diols.

<Experiment 3-6: N-Terminal Amino Acid Sequence>

Two purified preparations of PVA-degrading enzyme, PVA-A and PVA-B, obtained in Experiment 2 were subjected to N-terminal amino acid sequence analysis, and analyzed each amino acid sequence from the N-terminus to 20th residue. The N-terminal amino acid sequence analysis was carried out using "PPSQ-31A", a peptide sequencer manufactured by Shimadzu Corporation, Kyoto, Japan. As a result, it was revealed that PVA-A has an amino acid sequence of SEQ ID NO: 11, i.e., alanine-glutamic acid-asparagine-tryptophan-proline-methionine-phenylalanine-glycine-lysine-asparagine-tyrosine-glutamic acid-asparagine-threonine-arginine-alanine-threonine-serine-aspartic acid-threonine, as the N-terminal amino acid sequence. It was also revealed that PVA-B has an amino acid sequence of SEQ ID NO: 12, i.e., alanine-glutamic acid-asparagine-tryptophan-proline-methionine-phenylalanine-glycine-lysine-asparagine-tyrosine-glutamic acid-asparagine-serine-arginine-alanine-threonine-alanine-aspartic acid-threonine as the N-terminal amino acid sequence. Further, it was revealed that both enzymes have the same amino acid sequence from the N-terminus to 13th residue. i.e., SEQ ID NO: 1.

<Experiment 4: Whole Genome Sequencing of *Pseudomonas* sp. VT1B Strain (NBRC110478)>

In order to determine the nucleotide sequence of the DNA encoding the PVA-degrading enzyme of the present invention and the amino acid sequence of the PVA-degrading enzyme, *Pseudomonas* sp. VT1B strain (NBRC110478), producing the same enzyme, was subjected to whole genome sequencing.

<Experiment 4-1: Preparation of Genomic DNA>

*Pseudomonas* sp. VT1B strain (NBRC110478) subcultured on an agar plate was scraped with a platinum wire and inoculated into 3 mL of the liquid medium used in Experiment 1 in a test tube, and then cultured by shaking at 240 rpm at 27° C. for 5 days. After completion of the cultivation, cells were collected by centrifuging the culture, and the genomic DNA was prepared by conventional method using "DNeasy Blood & Tissue Kit", a commercially available total DNA purification kit, commercialized by QIAGEN N.V., Netherlands.

<Experiment 4-2: Determination of Whole Genomic Nucleotide Sequences Using a Next Generation Sequencer>

The genomic DNA obtained in Experiment 4-1 was enzymatically fragmented using "Nextera XT DNA Library Preparation Kit", a commercially available kit commercialized by Illumina Inc., California, USA, and the resulting DNA fragments were made into a library after modifying the ends of the DNA fragments to blunt ends and adding an adapter sequence to the ends, and then amplified by PCR and purified using "AMPure XP", a commercially available DNA purification kit commercialized by Beckman Coulter, Inc., California, USA. Successively, the nucleotide sequences of the library of DNA fragments were determined by using "MiSeq", a next-generation sequencer manufactured by Illumina Inc., California, USA, and the nucleotide sequence of each DNA fragment determined (Contig sequence) was integrated on a computer and the nucleotide sequence of whole genomic DNA was obtained.

Successively, the nucleotide sequence of the whole genomic DNA was analyzed by using "Glimmer", a gene region prediction software, and open reading frames (ORF: putative gene region) presumed to be encoding proteins were predicted. As a result, it was revealed that the whole genomic DNA of *Pseudomonas* sp. VT1B strain (NBRC110478) has 4,749 ORFs.

<Experiment 4-3: Identification of ORFs Encoding the PVA-Degrading Enzymes>

From the 4,749 ORFs found in the whole genome analysis of Experiment 4-2, ORFs encoding the amino acid sequences corresponding to the N-terminal amino acid sequences of the two PVA-degrading enzymes, PVA-A and PVA-B, determined in Experiment 3-2, were searched. As a result, it was revealed that the amino acid sequence completely matched to the N-terminal amino acid sequence of PVA-A was encoded by ORF3286, and that completely matched to the N-terminal amino acid sequence of PVA-B was encoded by ORF3283. From the result, it was revealed that the nucleotide sequence of ORF3286, i.e., the nucleotide sequence of SEQ ID NO: 4 is the structural gene DNA of PVA-A; and PVA-A consists of an amino acid sequence in which 26 amino acid residues at the N-terminal presumed to be a secretion signal sequence were removed from the amino acid sequence shown together with the nucleotide sequence of SEQ ID NO: 4, i.e., the amino acid sequence of SEQ ID NO: 2. Similarly, it was also revealed that the nucleotide sequence of ORF3283, i.e., the nucleotide sequence of SEQ ID NO: 5 is the structural gene DNA of PVA-B; and PVA-B consists of an amino acid sequence in which 26 amino acid residues at the N-terminal presumed to be a secretion signal sequence were removed from the amino acid sequence shown together with the nucleotide sequence of SEQ ID NO: 5, i.e., the amino acid sequence of SEQ ID NO: 3.

The molecular weight of PVA-A consisting of the amino acid sequence of SEQ ID NO: 2 was calculated to be 101,426. Also, the molecular weight of PVA-B consisting of the amino acid sequence of SEQ ID NO: 3 is calculated to be 109,679. The both molecular weights were well matched with the molecular weight of 100,000±20,000 obtained by SDS-PAGE in Experiment 3-1. The homology (sequence identity) between the amino acid sequence of PVA-A, SEQ ID NO: 2 and that of PVA-B, SEQ ID NO: 3 was examined using "GENETYX Ver. 13", a commercially available genetic information processing software, commercialized by Genetyx Corporation, Tokyo, Japan, and was calculated to be 84%. Similarly, the homology (sequence identity) between the nucleotide sequences of SEQ ID NO: 5 and SEQ ID NO: 6, encoding the respective enzyme, is calculated to be 82%.

<Experiment 5: Homology Search Based on Amino Acid Sequences of PVA-Degrading Enzymes>

Based on the amino acid sequences of PVA-A and PVA-B obtained in Experiment 4, i.e., the amino acid sequences of SEQ ID NO: 2 and SEQ ID NO: 3, a BLAST search was performed on a sequence database, GenBank. Surprisingly, it was found that the both amino acid sequences of PVA-A and PVA-B showed homology with the amino acid sequence of PVA dehydrogenase and that of oxidized PVA hydrolase, which are registered in GenBank and catalyzes completely different reactions each other. Further, it was also found that the amino acid sequences of these PVA-A and PVA-B were constructed by binding the N-terminal first half having a homology with PVA dehydrogenase and the C-terminal late half having a homology with oxidized PVA hydrolase via amino acid sequences having relatively low homology, predicted to be linkers.

Among the amino acid sequences of conventionally known enzymes which have been found in the above BLAST search to have homology with the PVA-degrading enzyme of the present invention, two amino acid sequences, that of PVA dehydrogenase from *Pseudomonas* sp. VM15C (GenBank accession No. BAA94193.1) and that of PVA dehydrogenase from *Sphingopyxis* sp. 113P3 (GenBank accession No. BAD95543.3) were selected as the amino acid sequences having relatively high homology with those of the N-terminal first half of PVA-A and PVA-B, and then the homology of the two amino acid sequences was investigated using "GENETYX Ver. 13", a genetic information processing software, commercialized by Genetyx Corporation, Tokyo, Japan.

As a result, the N-terminal first half (1st to 442nd residue) of the amino acid sequence of PVA-A, i.e. SEQ ID NO: 2, showed about 24% homology (sequence identity) to the amino acid sequence of PVA dehydrogenase (144th to 627th residue) from *Pseudomonas* sp. VM15C strain. Also, the same N-terminal first half (1st to 429th residue) showed about 26% homology (sequence identity) to the amino acid sequence of PVA dehydrogenase (151st to 627th residue) from *Sphingopyxis* sp. 113P3 strain.

On the other hand, the N-terminal first half (1st to 455th residue) of the amino acid sequence of PVA-B, i.e. SEQ ID NO: 3, showed about 23% homology (sequence identity) to the amino acid sequence of PVA dehydrogenase (144th to 630th residue) from *Pseudomonas* sp. VM15C strain. Also, the same N-terminal first half (1st to 455th residue) showed about 25% homology (sequence identity) to the amino acid sequence of PVA dehydrogenase (151st to 627th residue) from *Sphingopyxis* sp. 113P3 strain.

The multiple sequence alinement of 4 amino acid sequences, i.e., the amino acid sequences of the N-terminal first half of PVA-A and PVA-B, and the amino acid sequence of PVA dehydrogenases from *Pseudomonas* sp. VM15C strain and that from *Sphingopyxis* sp. 113P3 strain was shown in FIG. 7. It can be visually seen from FIG. 7 that the amino acid sequences of the N-terminal first half of PVA-A and PVA-B have low homology with the amino acid sequence of PVA dehydrogenase from *Pseudomonas* sp. VM15C strain or that from *Sphingopyxis* sp. 113P3 strain. These results suggest that the amino acid sequence of the N-terminal first half of the PVA-degrading enzyme of the present invention forms a domain having an activity of oxidizing PVA among the two activities possessed by the PVA-degrading enzyme.

In the same manner as examined for the amino acid sequence of the N-terminal first half, among the amino acid sequences of conventionally known enzymes which have been found in the above BLAST search to have homology with the PVA-degrading enzyme of the present invention, two amino acid sequences, that of oxidized PVA hydrolase from *Pseudomonas* sp. VM15C (GenBank accession No. BAA94192. 1) and that of oxidized PVA hydrolase from *Sphingopyxis* sp. 113P3 (GenBank accession No. BAD95542. 3) were selected as the amino acid sequences having relatively high homology with those of the C-terminal late half of PVA-A and PVA-B, and then the homology of the two amino acid sequences was investigated by the same manner.

As a result, the C-terminal late half (625th to 973rd residue) of the amino acid sequence of PVA-A, i.e. SEQ ID NO: 2, showed about 54% homology (sequence identity) to the amino acid sequence of oxidized PVA hydrolase (34th to 379th residues) from *Pseudomonas* sp. VM15C strain. Also, the same C-terminal late half (643rd to 973rd residue) showed about 55% homology (sequence identity) to the amino acid sequence of oxidized PVA hydrolase (39th to 363rd residue) from *Sphingopyxis* sp. 113P3 strain.

On the other hand, the C-terminal late half (586th to 963rd residue) of the amino acid sequence of PVA-B, i.e. SEQ ID NO: 3, showed about 50% homology (sequence identity) to the amino acid sequence of oxidized PVA hydrolase (3rd to 379th residue) from *Pseudomonas* sp. VM15C strain. Also, the same C-terminal late half (619th to 963rd residue) showed about 51% homology (sequence identity) to the amino acid sequence of oxidized PVA hydrolase (24th to 363rd residue) from *Sphingopyxis* sp. 113P3 strain.

The multiple sequence alinement of 4 amino acid sequences, i.e., the amino acid sequences of the C-terminal late half of PVA-A and PVA-B, and the amino acid sequence of oxidized PVA hydrolase from *Pseudomonas* sp. VM15C strain and that from *Sphingopyxis* sp. 113P3 strain, was shown in FIG. 8. It can be visually seen from FIG. 8 that the amino acid sequences of the C-terminal late half of PVA-A and PVA-B have respectively relatively high homology with the amino acid sequence of oxidized PVA hydrolase from *Pseudomonas* sp. VM15C strain or that from *Sphingopyxis* sp. 113P3 strain. These results suggest that the amino acid sequence of the C-terminal late half of the PVA-degrading enzyme of the present invention forms a domain having an activity of hydrolyzing oxidized PVA among the two activities possessed by the PVA-degrading enzyme.

Figure 9:
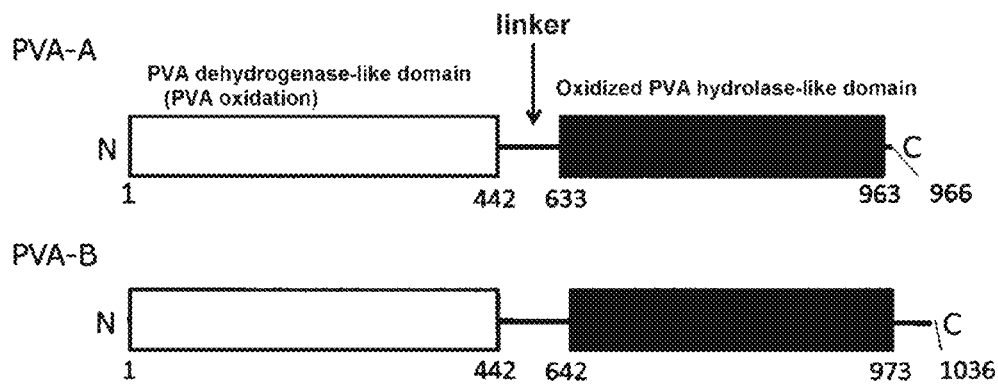
FIG. 9 is a diagram schematically showing the structure of two PVA-degrading enzyme, PVA-A and PVA-B.

The above findings are summarized, and the structures of PVA-A and PVA-B as PVA-degrading enzymes are schematically shown in FIG. 9. As shown in FIG. 9, the amino acid sequence of the N-terminal first half, 1 st to 442nd amino acid residues of the amino acid sequence of PVA-A (SEQ ID NO: 2) forms a domain catalyzing the oxidation of PVA and having a homology with the amino acid sequence of conventionally known PVA dehydrogenase, and the amino acid sequence of the C-terminal late half, 633rd to 963rd amino acid residues forms a domain catalyzing the hydrolysis of oxidized PVA and having a homology with the amino acid sequence of conventionally known oxidized PVA hydrolase, and the two domains were linked via a linker sequence with a length of about 90 amino acid residues. Almost the same structure was found in the case of the amino acid sequence of PVA-B (SEQ ID NO: 3).

<Experiment 9: Cloning of DNA Encoding PVA-Degrading Enzyme and Preparation of Recombinant DNA>

A DNA encoding PVA-A or PVA-B was respectively cloned by In-Fusion reaction of a DNA in which a portion presumed to be a secretion signal sequence of a PVA-degrading enzyme encoded by ORF3286 or ORF3283 was respectively deleted.

<Experiment 9-1: Cloning of DNA Encoding PVA-Degrading Enzyme and Preparation of Recombinant DNA>

At first, a linear pRSET A was prepared by PCR using the plasmid vector pRSET A as a template, and using Primer 1 and Primer 2, having the nucleotide sequence of SEQ ID NO: 6 and SEQ ID NO: 7, respectively, as primers. Successively, a DNA encoding PVA-A, i.e., a protein having an amino acid sequence in which the signal sequence is removed from the amino acid sequence encoded by ORF3286, was amplified by PCR using the genomic DNA as a template, and using Primer 3 and Primer 4, having the nucleotide sequence of SEQ ID NO: 8 and SEQ ID NO: 9, respectively, as primers. In the same manner, a DNA encoding PVA-B, i.e., a protein having an amino acid sequence in which the signal sequence is removed from the amino acid sequence encoded by ORF3283, was amplified by PCR using the genomic DNA as a template, and using Primer 3 and Primer 5, having the nucleotide sequence of SEQ ID NO: 8 and SEQ ID NO: 10, respectively, as primers.

The linear plasmid prepared above and PVA-A gene or PVA-B gene were subjected to In-Fusion reaction by using "In-Fusion HD Cloning Kit", a commercially available In-Fusion cloning kit commercialized by Takara Bio Inc., Shiga, Japan, to make into a recombinant plasmid, and named to "pRSET A-PVA-A" and "pRSET A-PVA-B", respectively. The structure of "pRSET A-PVA-A", a recombinant DNA encoding PVA-A, obtained by the above method was schematically shown in FIG. 10.

<Experiment 9-2: Preparation of a Transformant and Expression of PVA-Degrading Enzyme Protein>

Using "pRSET A-PVA-A", a recombinant DNA encoding PVA-A, obtained in Experiment 9-1, *E coli* HST08 was transformed by the conventional method and the recombinant DNA was prepared in large amount. When *E. coli* BL21 (DE3) was transformed by the recombinant DNA and the expression of the recombinant enzyme was tried, the formation of the expressed protein produced by expressing the recombinant DNA was observed.

<Experiment 10: Degradation of PVA by PVA-Degrading Enzyme>

Using the purified enzyme preparation of PVA-A obtained by the method of Experiment 2, the enzyme preparations varying the amount of enzyme were allowed to act on substrate solutions varying in PVA concentration, and the time course of the degradation of PVA was investigated by measuring the reduction of viscosity of the reaction mixture.

PVA as a substrate (Reagent grade polyvinyl alcohol, polymerization degree: 2,000, commercialized by Nacalai Tesque Inc., Kyoto, Japan), 50 mM sodium phosphate buffer (pH 7.0), and the purified enzyme solution of PVA-A dissolved in the same buffer were mixed, and the reaction mixtures (volume: 1 mL) with the final concentration of PVA of 1%, 4% or 10% (w/v), and the amount of PVA-A per 1 g-PVA of 1 (or 1.25), 5 or 10 units as PVA-oxidizing activity was prepared. Then, those reaction mixtures in plastic tubes were reacted with shaking at 160 rpm at 35° C. for 1, 4 or 20 hours. In each PVA concentration, a reaction mixture prepared by substituting the enzyme solution to 50 mM phosphate buffer (pH 7.0) was used as control (the amount of enzyme: zero unit). To viscosity measurement using "DV-II+Pro", a cone-plate viscometer manufactured by Brookfield, Boston, USA, 0.6 mL of a reaction mixture obtained by reacting under each condition was subjected. The viscosity of the reaction mixture under each reaction condition was shown in Table 4.

TABLE 4

| Concentration of PVA | Amount of enzyme | Viscosity of reaction mixture (mPa·s) Reaction Time (hour) | | | |
|---|---|---|---|---|---|
| (%, w/v) | (U/g-PVA) | 0 | 1 | 4 | 20 |
| 1 | 0 | 2.5 | 2.5 | 2.6 | 2.6 |
|   | 1.25 | 2.7 | 2.3 | 1.7 | 1.4 |
|   | 5 | 2.5 | 1.6 | 1.3 | 1.2 |
|   | 10 | 2.7 | 1.4 | 1.3 | 1.2 |
| 4 | 0 | 37.9 | 35.4 | 35.5 | 46.6 |
|   | 1 | 34.0 | 35.6 | 18.6 | 6.6 |
|   | 5 | 36.1 | 30.3 | 11.9 | 3.7 |
| 10 | 0 | 2480 | 2580 | 2700 | 2815 |
|   | 1 | 2530 | 1490 | 1550 | 873 |
|   | 5 | 2430 | 1520 | 769 | 231 |

As shown in Table 4, in any of the PVA concentration, in the case of allowing the PVA-degrading enzyme in an amount of 1 unit or higher as PVA-oxidizing activity per gram of PVA, the reduction of the viscosity of the PVA solution was observed. In the reaction using a PVA solution with a concentration of 1% (w/v) as the substrate, the viscosity of the PVA solution at the start of the reaction was 2.7 mPa·s, and the viscosity was decreased to 1.2 mPa·s after the reaction using the enzyme amount of 10 units for 20 hours (as a reference, the viscosity of purified water is about 1.0 mPa·s when measured under the same conditions). While, in the reaction using a PVA solution with a concentration of 4% (w/v) as the substrate, the viscosity of the PVA solution at the start of the reaction was about 36 mPa·s, and the viscosity was decreased to about ¹/₁₀, 3.7 mPa·s after the reaction using the enzyme amount of 5 units for 20 hours. Furthermore, the PVA-degrading enzyme, PVA-A, acts well on PVA even in a relatively high substrate concentration of 10% (w/v), and when PVA-A is allowed to act on PVA in an enzyme amount of 5 units per 1 g of PVA for 20 hours, the viscosity decreased from 2,430 mPa·s at the start of the reaction to about ¹/₁₀, 231 mPa·s.

While, the molecular weight of the degraded product of PVA was analyzed by conventional gel filtration HPLC for a reaction mixture obtained by allowing 10 units of the enzyme to act on 1% (w/v) PVA solution for 20 hours. Gel filtration HPLC was carried out using the following conditions:
Column: "TSKgel □-4000" (manufactured by Tosoh Corporation, Tokyo, Japan)
(Two columns were tandemly connected.);
Eluent: 50 mM phosphate buffer eluent (pH7.0);
Column temperature: 40° C.;
Flow rate: 0.5 mL/min;
Detector: "RID-20A", a differential refractometer, manufactured by Shimadzu Corporation, Kyoto, Japan.

The molecular weights of PVA and the degradation products of PVA were respectively calculated based on a calibration curve of molecular weights prepared by subjecting pullulan standards for molecular weight measurement, commercialized by Hayashibara Co., Ltd., Okayama, Japan, to gel filtration HPLC in the same manner. The gel filtration HPLC chromatogram of the reaction mixture (symbol "b" in FIG. 11) is shown in FIG. 11 in comparison with that of PVA used as a substrate (symbol "a" in FIG. 11).

Figure 11:
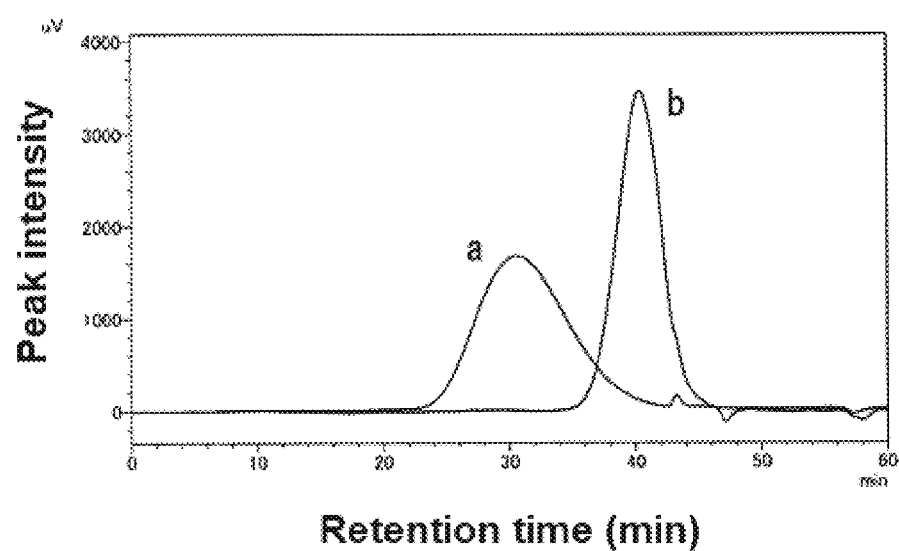
FIG. 11 is a gel filtration chromatogram of PVA degradation products obtained by allowing a PVA-degrading enzyme, PVA-A, to act on the substrate, PVA.

As shown in FIG. 11, in the case of PVA used as the substrate (Symbol "a"), PVA showed a peak top at retention time 30.6 min in its chromatogram and its weight average molecular weight (Mw) was calculated to be about $10.6 \times 10^4$. In the case of the reaction mixture of PVA degradation (Symbol "b"), obtained by allowing 10 units of the enzyme to act on 1% (w/v) solution of PVA for 20 hours, the degraded products showed a peak top at retention time 40.4 min in its chromatogram and its weight average molecular weight (Mw) was calculated to be about 4,400. From the results, it was revealed that, in the reaction mixture of PVA degradation, PVA as a substrate was degraded to products with low molecular weights by PVA-A.

As described above, PVA-degrading enzyme of the present application is solely able to degrade PVA efficiently. Since the PVA-degrading enzyme of the present invention is a hybrid enzyme having both PVA-oxidizing activity and oxidized PVA-hydrolyzing activity, this has become possible for the first time.

<Experiment 11: Detection of PVA Oxidase Fragment and Oxidized PVA Hydrolase Fragments>

In the fractions obtained by CM-TOYOPEARL column chromatography in the purification step of PVA-A and PVA-B in Experiment 2, fractions having the PVA-oxidizing activity, other than PVA-A and PVA-B, were observed. When the fraction was subjected to SDS-polyacrylamide gel electrophoresis as in Experiment 3, a protein band having a molecular weight of about 50,000, lower than those of PVA-A and PVA-B, was detected. When the N-terminal amino acid sequence of the protein was determined 20 residues from N-terminus by the same method in Experiment 3-6, it was revealed that the protein has the identical amino acid sequence with PVA-A, i.e., alanine-glutamic acid-asparagine-tryptophan-proline-methionine-phenylalanine-glycine-lysine-asparagine-tyrosine-glutamic acid-asparagine-threonine-arginine-alanine-threonine-serine-aspartic acid-threonine. Although the detailed data is omitted, the fractions exhibiting PVA-oxidizing activity showed no activity of hydrolyzing oxidized PVA. This result indicates that the enzyme having PVA-oxidizing activity in the fraction is a PVA-oxidizing enzyme fragment derived from PVA-A, having only PVA-oxidizing activity.

Similarly, in the fractions obtained by CM-TOYOPEARL column chromatography in the purification step of PVA-A and PVA-B in Experiment 2, fractions having the oxidized PVA-hydrolyzing activity and being different from PVA-A and PVA-B, were also observed. When the fraction was subjected to SDS-polyacrylamide gel electrophoresis, a protein band having a molecular weight of about 35,000, lower than those of PVA-A and PVA-B, was detected. When the N-terminal amino acid sequence of the protein was determined by the same method in Experiment 3-6, 5 amino acid residues could be determined and the N-terminal amino acid sequence was valine-serine-glycine-glycine-threonine. The amino acid sequence was completely matched with the amino acid sequence from 623rd to 627th amino acid residues of SEQ ID NO 2, i.e., the amino acid sequence of PVA-A. It was considered that the protein having the molecular weight of about 35,000 and the amino acid sequences from 623rd to 627th amino acid residues of the amino acid sequence of PVA-A is an oxidized PVA-hydrolyzing enzyme fragment derived from PVA-A, having only oxidized PVA-hydrolyzing activity, in combination with the knowledges shown in FIG. 8 comparing the amino acid sequences of PVA-A and PVA-B with those of conventionally known oxidized PVA hydrolases, and FIG. 9 schematically showing the structures of PVA-A and PVA-B.

The above results indicate that, in the culture of *Pseudomonas* sp. VT1B strain (NBRC110478), at least PVA-A, one of the PVA-degrading enzymes produced as a hybrid enzyme having both PVA-oxidizing activity and PVA-hydrolyzing activity, is partially hydrolyzed to form a PVA-oxidizing enzyme fragment and an oxidized PVA-hydrolyzing enzyme fragment. Based on the results, it is suggested that a PVA-oxidizing enzyme and an oxidized PVA-hydrolyzing enzyme can be separately prepared by artificially and partially degrading PVA-A or PVA-B as a hybrid enzyme.

The following examples explain the present invention in more detail. However, the present invention is not restricted by them.

Example 1

<Preparation of PVA-Degrading Enzyme>

A liquid culture medium comprising 1 g/L of PVA (Reagent grade polyvinyl alcohol, polymerization degree: 500, commercialized by Nacalai Tesque Inc., Kyoto, Japan), 1 g/L of potassium phosphate, 0.5 g/L of sodium chloride, 4 g/L of ammonium nitrate, 0.5 g/L of magnesium sulfate 7 hydrate, 0.5 g/L of yeast extract (Yeast extract D-3H, commercialized by Nihon Pharmaceutical Co., Ltd., Tokyo, Japan) and water was adjusted to pH 7.0 and then sterilized by autoclaving at 121° C. for 20 min. Successively, pyrroloquinoline quinone (PQQ) sterilized by filtration was admixed with the culture medium to give a final concentration of 10 □g/L, and the resulting culture medium was used for cultivation.

*Pseudomonas* sp. VT1B strain was cultured in the same method in Experiment 1 as a seed culture, and then the seed culture was inoculated to 50 mL of the above liquid medium dispensed in a 500 mL-volume of Erlenmeyer flask in an amount of 1% (w/v) of the liquid medium, and cultured with stirring at 240 rpm, 27° C. for 5 days. The PVA-degrading enzyme activity of the culture supernatant obtained after the cultivation was 0.034 unit/mL as PVA-oxidizing activity. While, acetone, a hydrolysis product was detected when the culture supernatant was allowed to act on 2, 4-pentanedione. Accordingly, it was confirmed that the culture supernatant also has a β-diketone-hydrolyzing activity, i.e., an oxidized PVA-hydrolyzing activity. The culture supernatant can be advantageously used as a crude enzyme preparation of PVA-degrading enzyme.

Example 2

<PVA-Degrading Enzyme Preparation>

About 1 L of culture of *Pseudomonas* sp. VT1B strain, obtained by the method of Example 1, was centrifuged at 10,000 rpm for 30 min, and about 960 mL (PVA oxidizing activity: about 32 units) of culture supernatant was obtained. Then, ammonium sulfate was added to the culture supernatant to give a concentration of 25%-saturation and dissolved, and then the resulting solution was stood in a cold chamber for one night. The resulting precipitate was collected by centrifugation, dissolved in 10 mM phosphate buffer (pH 7.0), and dialyzed against the same buffer. The resulting dialyzed solution was subjected to SDS-PAGE by the method in Experiment 3-1, and as a result, a single protein band exhibiting the molecular weight of 100,000±20,000 was detected, revealing that concomitant proteins detected in the culture supernatant were almost removed. It was revealed that the PVA-degrading enzyme can be purified efficiently by the purification procedure. Since the resulting partially purified preparation of PVA-degrading enzyme showed β-diketone-hydrolyzing activity, i.e., oxidized PVA-hydrolyzing activity in addition to PVA-oxidizing activity, it can be advantageously used as a PVA-degrading enzyme.

Example 3

<PVA-Degrading Enzyme Preparation>

About 600 mL of culture of *Pseudomonas* sp. VT1B strain, obtained by the method of Example 1, was centrifuged at 10,000 rpm for 30 min, and about 560 mL (PVA-oxidizing activity: about 19.1 units) of culture supernatant was obtained. Then, ammonium sulfate was added to the culture supernatant to give a concentration of 60%-saturation and dissolved, and then the resulting solution was stood in a cold chamber for one night. The resulting precipitate was collected by centrifugation, dissolved in 5 mM phosphate buffer (pH 7.0), and dialyzed against the same buffer. The resulting dialyzed solution was subjected to a liquid chromatography using a column packed with "TOYOPEARL AF-Blue F3GA" (Functional group: Cibacron Blue F3GA) and pre-equilibrated with the same buffer. The adsorbed proteins were eluted by using a linear gradient of potassium chloride (KCl) from zero to 1 M. The PVA-degrading enzyme was eluted at KCl concentration of about 0.2 M, and the active fractions were collected and made into a partially purified PVA-degrading enzyme preparation. Since the resulting partially purified preparation of PVA-degrading enzyme showed pi-diketone-hydrolyzing activity, i.e., oxidized PVA-hydrolyzing activity in addition to PVA-oxidizing activity, it can be advantageously used as a PVA-degrading enzyme.

INDUSTRIAL APPLICABILITY

According to the present invention, it is possible to produce in an industrial scale and provide a PVA-degrading enzyme, having both PVA-oxidizing activity and oxidized PVA-hydrolyzing activity, as a completely novel hybrid enzyme which has ever been unknown. The present invention, which enables to provide the completely novel PVA-degrading enzyme, contributes to various fields requiring the degradation and elimination of PVA, and therefore, its industrial significance is very large.

EXPLANATION OF SYMBOLS

Figure 10:
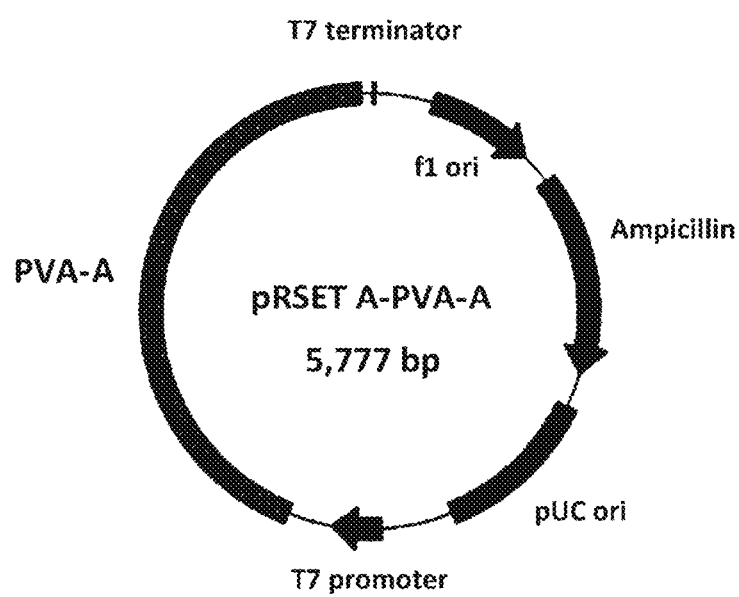
FIG. 10 is a schematic diagram showing the structure of "pRSET A-PVA-A", an autonomously replicable recombinant DNA comprising a DNA encoding a PVA-degrading enzyme, PVA-A.

In FIG. 2,

M: Molecular weight marker;

A: Purified PVA-degrading enzyme preparation, PVA-A:

B: Purified PVA-degradation enzyme preparation, PVA-B;

In FIGS. 4 and 6,

■: Acetate buffer;

●: Phosphate buffer;

▲: Glycine-NaOH buffer;

♦: Potassium chloride-NaOH buffer;

In FIGS. 7 and 8, amino acid residues are denoted by one letter notation, amino acid residues shaded in gray means an amino acid residue that is matched in three of the four amino acid sequences compared, and amino acid residues shaded with black means an amino acid residue that is consistent with all four amino acid sequences.
PVA-A: Amino acid sequence of PVA-A (SEQ ID NO: 2);
PVA-B: Amino acid sequence of PVA-B (SEQ ID NO: 3);
PVADH_VM15C: Amino acid sequence of PVA dehydrogenase derived from *Pseudomonas* sp. VM15C;
PVADH_113P3: Amino acid sequence of PVA dehydrogenase derived from *Sphingopyxis* sp. 113P3;
OPH_VM15C: Amino acid sequence of oxidized PVA hydrolase derived from *Pseudomonas* sp. VM15C;
OPH_113P3: Amino acid sequence of oxidized PVA hydrolase derived from *Sphingopyxis* sp. 113P3;

In FIG. 9,
The number means the amino acid residue number;
N: N-terminus;
C: C-terminus;
In FIG. 10,
f1 ori: f1 phage replication origin;
Ampicillin: ampicillin resistant gene;
pUC ori: pUC replication origin;
PVA-A: PVA-A gene;
In FIG. 11,
a: Gel filtration HPLC chromatogram of PVA used as a substrate;
b: Gel Filtration HPLC chromatogram of PVA degradation products;

What is claimed is:

1. A process for producing a polyvinyl alcohol-degrading enzyme, comprising the steps of:
   culturing a microorganism capable of producing the polyvinyl alcohol-degrading enzyme in a nutrient medium;
   removing cells from the resulting culture to obtain a supernatant; and
   collecting the polyvinyl alcohol-degrading enzyme from the supernatant or collecting the supernatant as a crude enzyme preparation containing the polyvinyl alcohol-degrading enzyme;
   wherein said polyvinyl alcohol-degrading enzyme comprises the following characteristics (1) to (3):
   (1) comprising an activity of oxidizing polyvinyl alcohol and forming hydrogen peroxide;
   (2) comprising an activity of hydrolyzing β-diketone; and
   (3) exhibiting a molecular weight of 100,000±20,000 in SDS-polyacrylamide gel electrophoresis,
   and wherein said polyvinyl alcohol-degrading enzyme comprises the amino acid sequence of SEQ ID NO: 2 or SEQ ID NO: 3, or an amino acid sequence comprising a deletion, a replacement, or an addition of one or more amino acid residues in the amino acid sequence of SEQ ID NO: 2 or SEQ ID NO: 3 while retaining the polyvinyl alcohol-degrading activity and comprising 84% or higher sequence identity to the amino acid sequence of SEQ ID NO: 2 or SEQ ID NO: 3.

2. The process of claim 1, wherein said activity of oxidizing polyvinyl alcohol comprises the following characteristics (4) to (7):
   (4) Optimum temperature:
      35 to 40° C. under the conditions of 60 min-reaction at pH 7.0;
   (5) Optimum pH:
      pH 6.5 to 8.0 under the conditions of 60 min-reaction at 27° C.;
   (6) Thermal stability:
      Stable up to 45° C. under the conditions of holding for 60 min at pH 7.0; and
   (7) pH stability:
      Stable in a range of pH 4.5 to 10.5 under the condition of holding for 24 hours at 4° C.

3. The process of claim 1, wherein said polyvinyl alcohol-degrading enzyme further comprises the following characteristic (8):
   (8) comprises the amino acid sequence of SEQ ID NO: 1 as the N-terminal amino acid sequence.

4. The process of claim 1, wherein said polyvinyl alcohol-degrading enzyme is encoded by the nucleotide sequence of SEQ ID NO: 4 or SEQ ID NO: 5, or a nucleotide sequence comprising a deletion, a replacement, or an addition of one or more nucleotides in the nucleotide sequence of SEQ ID NO: 4 or SEQ ID NO: 5 while retaining the encoded polyvinyl alcohol-degrading activity and having 82% or higher sequence identity to the nucleotide sequence of SEQ ID NO: 4 or SEQ ID NO: 5, or complementary nucleotide sequences thereof.

5. The process of claim 1, wherein said microorganism belongs to the genus *Pseudomonas*.

6. A process for producing a recombinant polyvinyl alcohol-degrading enzyme, comprising the steps of:
   transforming a microorganism by introducing a replicable recombinant DNA, which comprises a DNA encoding a polyvinyl alcohol-degrading enzyme and an autonomously replicable vector, into the microorganism to obtain a transformant capable of expressing the polyvinyl alcohol-degrading enzyme encoded by the DNA;
   culturing the transformant in a nutrient medium; and
   collecting the recombinant polyvinyl alcohol-degrading enzyme from the resulting culture,
   wherein said recombinant polyvinyl alcohol-degrading enzyme comprises the following characteristics (1) to (3):
   (1) comprising an activity of oxidizing polyvinyl alcohol and forming hydrogen peroxide;
   (2) comprising an activity of hydrolyzing β-diketone; and
   (3) exhibiting a molecular weight of 100,000±20,000 in SDS-polyacrylamide gel electrophoresis,
   and wherein said polyvinyl alcohol-degrading enzyme comprises the amino acid sequence of SEQ ID NO: 2 or SEQ ID NO: 3, or an amino acid sequence comprising a deletion, a replacement, or an addition of one or more amino acid residues in the amino acid sequence of SEQ ID NO: 2 or SEQ ID NO: 3 while retaining the polyvinyl alcohol-degrading activity and comprising 84% or higher (sequence identity to the amino acid sequence of SEQ ID NO: 2 or SEQ ID NO: 3.

7. The process of claim 6, wherein said activity of oxidizing polyvinyl alcohol comprises the following characteristics (4) to (7):
   (4) Optimum temperature:
      35 to 40° C. under the conditions of 60 min-reaction at pH 7.0;
   (5) Optimum pH:
      pH 6.5 to 8.0 under the conditions of 60 min-reaction at 27° C.;
   (6) Thermal stability:
      Stable up to 45° C. under the conditions of holding for 60 min at pH 7.0; and
   (7) pH stability:
      Stable in a range of pH 4.5 to 10.5 under the condition of holding for 24 hours at 4° C.

8. The process of claim 6, wherein said DNA encodes a polyvinyl alcohol-degrading enzyme comprising the amino acid sequence of SEQ ID NO: 1 as the N-terminal amino acid sequence.

9. The process of claim 6, wherein said DNA comprises the nucleotide sequence of SEQ ID NO: 4 or SEQ ID NO: 5, or a nucleotide sequence comprising a deletion, a replacement, or an addition of one or more nucleotides in the nucleotide sequence of SEQ ID NO: 4 or SEQ ID NO: 5 while retaining the encoded polyvinyl alcohol-degrading activity and having 82% or higher sequence identity to the nucleotide sequence of SEQ ID NO: 4 or SEQ ID NO: 5, or complementary nucleotide sequences thereof.

10. The process of claim 6, wherein said DNA is obtainable by replacing one of more nucleotides of SEQ ID NO:

4 or SEQ ID NO: 5 with other nucleotides without altering the amino acid sequence encoded thereby based on the degeneracy of genetic code.

\* \* \* \* \*